US012633414B1

(12) United States Patent
Lee

(10) Patent No.: US 12,633,414 B1
(45) Date of Patent: May 19, 2026

(54) SAFETY RECEIPT LAYER FOR PERMIT-BEFORE-ACTION GATING OF AI-ASSISTED CLINICAL DECISION SUPPORT INTERVENTIONS

(71) Applicant: Yong Bok Lee, Sheridan, WY (US)

(72) Inventor: Yong Bok Lee, Sheridan, WY (US)

(73) Assignee: Light & Salt LLC, Sheridan, WY (US)

( * ) Notice: Subject to any disclaimer, the term of this patent is extended or adjusted under 35 U.S.C. 154(b) by 0 days.

(21) Appl. No.: 19/416,091

(22) Filed: Dec. 11, 2025

Related U.S. Application Data

(60) Provisional application No. 63/926,585, filed on Nov. 27, 2025.

(51) Int. Cl.
    *G16H 50/20*     (2018.01)
    *G16H 10/60*     (2018.01)
    *G16H 30/40*     (2018.01)
    *H04L 9/32*     (2006.01)

(52) U.S. Cl.
    CPC ............. *G16H 50/20* (2018.01); *G16H 10/60* (2018.01); *G16H 30/40* (2018.01); *H04L 9/3242* (2013.01)

(58) Field of Classification Search
    CPC ........ G16H 50/20; G16H 10/60; G16H 30/40; H04L 9/3242
    See application file for complete search history.

(56) References Cited

U.S. PATENT DOCUMENTS

| | | | | |
|---|---|---|---|---|
| 5,924,074 A * | 7/1999 | Evans | .................... | G16H 20/10 |
| | | | | 707/999.001 |
| 6,650,964 B2 * | 11/2003 | Spano, Jr. | .............. | G16H 10/60 |
| | | | | 700/244 |
| 7,587,368 B2 * | 9/2009 | Felsher | ............... | G06F 21/6245 |
| | | | | 705/52 |

(Continued)

OTHER PUBLICATIONS

ONC, "Health Data, Technology, and Interoperability (HTI-1) Final Rule," 89 Fed. Reg. 1192-1438, Jan. 9, 2024.

(Continued)

*Primary Examiner* — J. Brant Murphy

(57) ABSTRACT

A safety receipt layer is interposed between an electronic health record (EHR) system and clinical decision support intervention (DSI) engines, including AI-assisted DSIs. For each DSI episode, the layer constructs a canonical clinical context envelope, evaluates a policy graph, and computes a permit outcome (permit, guarded permit, override, deny) that is enforced in a permit-before-action, fail-closed configuration. A time-of-check-to-time-of-use latch binds policy evaluation and any anchoring precondition to rendering and EHR write-back so outputs cannot be finalized without an affirmative permit or recorded override. The layer emits a structured, machine-verifiable safety receipt encoding policy identifiers, the context envelope or a cryptographic digest of a canonicalized field list, the permit outcome, requested and effective behavior modes, and clinician response. Receipts are anchored in an append-only verifiable log with maximum-merge-delay signed heads and (Continued)

t₄: Permit or Override Decision

↳ Trigger Receipt Construction

Safety Receipt Generator [138]

↳ Construct Receipt

Safety Receipt [400]
• Receipt ID, Timestamp
• Patient ID (hashed)
• DSI Type, Outcome
• Policy Version, Override Info
• Clinician Response ↳ Send to Anchor     ↳ Redacted Views PoPC Anchor Client [140]     Role-Based Receipt Views (clinician, analyst, payer, regulator)

↳ Audit Store

Anchor to Audit Store(s) (EHR log, compliance lake, external append-only log)

inclusion and consistency proofs, enabling verification, role-based views, monitoring, and mappings to health IT transparency or certification requirements.

30 Claims, 8 Drawing Sheets

(56) References Cited

U.S. PATENT DOCUMENTS

| | | | | |
|---|---|---|---|---|
| 7,730,528 | B2 * | 6/2010 | Chun | H04L 67/565 |
| | | | | 726/3 |
| 7,810,142 | B2 * | 10/2010 | Agrawal | G06F 21/6245 |
| | | | | 726/5 |
| 8,498,941 | B2 | 7/2013 | Felsher | |
| 8,504,392 | B2 * | 8/2013 | Saria | G16H 15/00 |
| | | | | 706/45 |
| 8,527,293 | B2 | 9/2013 | Hammond et al. | |
| 8,600,895 | B2 | 12/2013 | Felsher | |
| 8,738,396 | B2 * | 5/2014 | Green, III | G16H 10/20 |
| | | | | 705/2 |
| 8,745,085 | B2 * | 6/2014 | Fabbri | G16H 10/60 |
| | | | | 707/776 |
| 10,123,729 | B2 * | 11/2018 | Dyell | A61B 5/162 |
| 11,967,427 | B2 * | 4/2024 | Willard | G16H 10/60 |
| 12,381,773 | B2 * | 8/2025 | Damodaran | G06N 20/00 |
| 12,542,216 | B2 * | 2/2026 | Arkoff | G16H 50/30 |
| 2002/0040282 | A1 * | 4/2002 | Bailey | G16H 50/20 |
| | | | | 702/188 |
| 2002/0046346 | A1 | 4/2002 | Evans | |
| 2007/0112782 | A1 * | 5/2007 | Lobach | G16H 70/20 |
| 2008/0243542 | A1 * | 10/2008 | Hammond | G16H 50/20 |
| | | | | 705/2 |
| 2010/0241595 | A1 * | 9/2010 | Felsher | G16H 10/65 |
| | | | | 707/E17.014 |
| 2011/0301982 | A1 * | 12/2011 | Green, Jr. | G16H 40/67 |
| | | | | 705/3 |
| 2015/0058627 | A1 * | 2/2015 | Paffel | G16H 10/60 |
| | | | | 713/168 |
| 2019/0348163 | A1 * | 11/2019 | Kantrowitz | G06N 5/02 |
| 2023/0069416 | A1 * | 3/2023 | Walker | G06Q 20/14 |
| 2025/0285761 | A1 * | 9/2025 | McNair | G16H 10/60 |
| 2025/0378923 | A1 * | 12/2025 | Macoviak | G16H 10/60 |
| 2026/0024668 | A1 * | 1/2026 | Arkoff | G16H 50/30 |

OTHER PUBLICATIONS

ONC, "HTI-1 Final Rule Overview Fact Sheet," Dec. 2023.
NIST, SP 800-53 Rev.5: Security and Privacy Controls for Information Systems and Organizations, Sep. 2020.
IHE International, ITI Technical Framework, vol. 1: Integration Profiles (Rev.17.0—Final Text)—Ch.9 ATNA, Jul. 20, 2020.
European Parliament and Council, "Artificial Intelligence Act, Reg. (EU) 2024/1689," OJ L, Jul. 12, 2024.
IMDRF, "Good Machine Learning Practice for Medical Device Development: Guiding Principles," IMDRF/AIML WG/N88, Jan. 29, 2025.
FDA, "Clinical Decision Support Software: Guidance for Industry and FDA Staff," Sep. 28, 2022.
FDA, "AI/ML-Based Software as a Medical Device (SaMD): Discussion Paper and Request for Feedback," Jan. 2021.
NIST, "Artificial Intelligence Risk Management Framework (AI RMF 1.0)," NIST AI 100-1, Jan. 2023.
U.S. Dept. of Health & Human Services, "45 C.F.R. § 164.308—Administrative safeguards.".
HL7, "FHIR Release 4—AuditEvent Resource," HL7 FHIR R4.
Woo, M.; Bacon, O., "Alarm Fatigue," in Making Healthcare Safer III, AHRQ, 2020.
AHRQ Patient Safety Network, "Alert Fatigue—Patient Safety Primer," PSNet, 2024.
The Joint Commission, "Medical Device Alarm Safety in Hospitals," Sentinel Event Alert 50, Apr. 8, 2013.
Ruskin, K.J.; Bliss, J.P., "Alarm Fatigue and Patient Safety," Anesth. Patient Saf. Found. Newsl., 34(1), 2019.
Cardoso, M.J., Moosbauer, J., Cook, T.S., et al., "RAISE—Radiology AI Safety, an End-to-Lifecycle Approach," arXiv:2311. 14570, Nov. 2023.
Yi, P.H., Haver, H.L., Jeudy, J.J., et al., "Best Practices for the Safe Use of Large Language Models and Other Generative AI in Radiology," Radiology 316(3), 2025.
Aldhafeeri, F.M., "Governing Artificial Intelligence in Radiology: Systematic Review," Diagnostics 15(18):2300, 2025.
Geis, J.R., Brady, A.P., Wu, C.C., et al., "Ethics of Artificial Intelligence in Radiology: Multisociety Statement," Can. Assoc. Radiol. J. 70(4):329-334, 2019.

* cited by examiner

SAFETY RECEIPT LAYER FOR PERMIT-BEFORE-ACTION GATING OF AI-ASSISTED CLINICAL DECISION SUPPORT INTERVENTIONS

As used herein, "HTI safety receipt layer" or "HTI-Ready Safety Receipt Layer" denotes the disclosed safety receipt architecture interposed between an EHR system and one or more clinical decision support intervention (DSI) engines and configured to capture clinical context, evaluate a policy graph, enforce permit-before-action semantics, and generate structured safety receipts for DSI episodes.

Non-Trademark & Terminology Notice (illustrative; non-limiting). "HTI-Ready Safety Receipt Layer," "HTI safety receipt layer," "clinical decision support intervention (DSI)," "proof-of-policy-compliance (PoPC)," "Sensor Receipt (S2)," "Reality Receipt (R2)," "Safety Evidence Receipt," and similar acronyms used herein are technical labels for clarity. They carry no trademark significance, and unless expressly stated otherwise, the scope of the invention is defined by the claims and the written description.

Appendix A (Glossary) forms part of this Specification and provides definitions and illustrative synonyms for terms used herein. Examples and synonyms in Appendix A are illustrative and non-limiting; unless expressly stated otherwise, the scope of the invention is defined by the claims and the written description, and not by labels or examples in the Glossary.

II. CROSS-REFERENCE TO RELATED APPLICATIONS

Related applications and evidence-only interoperation (illustrative; non-limiting; no admission). In some embodiments, the safety receipt layer can interoperate with one or more co-pending applications by the same inventor(s) directed to: (i) intent settlement layers and proof-of-policy-compliance (PoPC) receipts for autonomous or semi-autonomous actions; (ii) clinical override control and structured override receipts; (iii) therapeutic episode capture and anonymized evidence libraries; (iv) governance rails for decision-support services; (v) trusted sensor ingress layers that gate sensor or imaging data and emit per-event sensor receipts; (vi) operating-system reality compositor rails that gate rendering of synthetic overlays based on per-overlay reality receipts; and (vii) multi-harm safety risk-budget engines that aggregate harm-specific signals across AI safety episodes and emit structured Safety Evidence Receipts suitable for oversight and post-deployment monitoring. To the extent permitted, each such application is incorporated by reference for non-essential subject matter only under 37 C.F.R. § 1.57; all essential material supporting the claims is provided expressly herein, and in the event of any inconsistency the present disclosure controls. Cross-rail references are illustrative and evidentiary only and do not alter the permit-before-action semantics or fail-closed behavior enforced by the safety receipt layer; the claims control. The identification of any document or application herein is not an admission that it constitutes prior art.

Priority and incorporation (illustrative; non-limiting). This application claims the benefit of U.S. Provisional Patent Application No. 63/926,585, filed Nov. 27, 2025, under 35 U.S.C. § 119 (e), to the extent permitted. The disclosure of the provisional application is incorporated by reference for non-essential subject matter only, consistent with 37 C.F.R. § 1.57. In the event of any inconsistency between the provisional application and the present disclosure, the present disclosure controls; all essential material supporting the claims is provided explicitly herein.

Related applications (informative; non-limiting). Applicants may file additional applications describing other governance rails or operating layers that interoperate with the safety receipt layer via evidence objects such as permit identifiers, safety receipt references, or cross-rail receipt pointers (for example, trusted sensor ingress rails, trusted reality compositor rails, or safety risk budget engines). This Specification stands on its own and does not alter the internal gate semantics of any such related rails; any related filings are complementary and evidence-only with respect to the present safety receipt layer.

Cross-rail interoperation notice (illustrative; non-limiting). The HTI safety receipt layer may interoperate with external governance rails such as trusted sensor ingress rails (for example, a TSIL or TSIL-Scan medical-imaging ingress gateway that emits Sensor Receipts (S2)), trusted reality compositor rails (for example, a Trusted Reality Compositor (TRC) that gates rendering of synthetic overlays under per-overlay Reality Receipts (R2)), Safety Risk Budget Engines that emit Safety Evidence Receipts, and revenue-cycle governance rails that emit Revenue Cycle Truth Receipts. Such interoperation references are illustrative and evidentiary only and do not alter the permit-before-action semantics, permit outcomes, or fail-closed behavior enforced by the safety receipt layer; the claims control.

Appendices as part of the Specification (illustrative; evidence-only). Appendices A-E form part of this Specification and provide, by way of example and not limitation, glossary entries, example safety receipt schemas, transparency and certification mappings, policy graph sketches, and reference deployment profiles. These materials aid enablement, conformance, and procurement and are illustrative and evidence-only; the claims control, and permit-before-action and fail-closed gate predicates remain defined in the core Specification.

III. FIELD

The present disclosure relates generally to computer-implemented healthcare information systems and health information technology (health IT) governance. More particularly, it relates to systems and methods that implement a safety receipt layer interposed between electronic health record (EHR) systems and one or more clinical decision support intervention (DSI) engines, including AI-assisted, rules-based, and other algorithmic or protocol-driven DSIs. The safety receipt layer is configured to capture clinical context, evaluate governance policies, and emit structured, machine-verifiable safety receipts for DSI episodes in coordination with other health IT modules within clinical workflows.

IV. BACKGROUND

Modern electronic health record (EHR) and health IT platforms increasingly embed AI-assisted decision support interventions (DSIs), including rules-based alerts, machine learning-based risk scores, and large language model (LLM)-based recommendations. Such DSIs may suggest diagnoses, order sets, dosages, triage or admit/discharge decisions, or multi-step care pathways and treatment plans (for example, oncology treatment regimens or chronic disease management plans) based at least in part on patient-specific data stored in the EHR or associated systems.

Examples of DSIs further include technology-enabled chronic disease management interventions, remote monitoring programs, and digital coaching workflows in which AI-assisted recommendations, alerts, or multi-step care plans are delivered over time for patients with conditions such as hypertension, diabetes, heart failure, or chronic pain.

One concrete class of DSIs includes imaging-based triage models that ingest one or more radiology images and attempt, in a single pass, to detect or prioritize multiple urgent findings for review. For example, an abdomen-pelvis computed tomography (CT) triage model may be configured to flag suspected small bowel obstruction, acute cholecystitis, acute pancreatitis, acute diverticulitis, hydronephrosis, free air, or an unruptured abdominal aortic aneurysm for expedited interpretation.

Such multi-condition imaging DSIs may operate in high-throughput emergency care environments and may strongly influence downstream clinical decisions, including radiology worklist prioritization, activation of surgical or interventional teams, and admit, discharge, or transfer decisions. However, conventional EHR and picture archiving and communication system (PACS) integrations for these imaging DSIs often lack structured safety receipts that represent the full DSI episode context, applicable policies, and clinician responses, making it difficult for health systems, payers, and regulators to audit real-world DSI behavior and safety.

Another rapidly evolving class of DSIs comprises AI-based chest radiograph analyzers that attempt to prioritize or interpret thoracic imaging studies, such as chest x-rays acquired in emergency or inpatient settings. Such DSIs may generate triage flags, structured labels for multiple target conditions, or draft radiology reports and patient-facing explanations in a largely automated fashion.

Vendors and health systems may be tempted to deploy such chest-radiograph DSIs in near-autonomous configurations, for example by automatically labeling apparently normal studies as "no actionable finding," auto-populating report text, or triggering downstream care pathways with limited human review. However, without a structured, episode-level representation of applicable policies, permit outcomes, and clinician responses, it may be difficult for health systems, payers, regulators, or courts to determine how responsibility and oversight were maintained and whether the DSI was used within its intended indications, particularly when autonomous behaviors are enabled or suspended over time.

Another emerging class of imaging-based DSIs comprises digital pathology decision support systems that ingest whole-slide imaging (WSI) studies or other pathology images acquired by high-throughput scanners in anatomic pathology laboratories. Such DSIs may, for example, propose case-level triage rankings, highlight regions of interest, estimate tumor burden or margin status, compute standardized scoring outputs for one or more biomarkers, or generate draft pathology reports or synoptic summaries for review by a pathologist. As with radiology-focused imaging DSIs, conventional integrations of digital pathology DSIs with pathology viewers, laboratory information systems (LIS), or EHR systems often lack structured, episode-level safety receipts tied to applicable policies, permit outcomes, and pathologist responses, making it difficult for health systems, payers, and regulators to audit real-world behavior and to determine whether autonomous or semi-autonomous digital pathology workflows remained within intended indications, validation boundaries, and governance constraints.

Another emerging class of decision support interventions comprises AI-assisted intra-body robotic navigation and intervention systems. Such systems may coordinate or control ingestible capsule robots, catheter-based robots, steerable endoscopes, or other intra-luminal or intra-vascular robotic devices that acquire imaging or physiologic data and, in some configurations, perform local therapeutic actions such as biopsy, ablation, drug delivery, or mechanical thrombectomy. When deployed in near-autonomous or semi-autonomous modes, these intra-body robotic DSIs may propose, sequence, or execute physical actions inside the body based at least in part on patient-specific data and learned policies, creating high-consequence safety and accountability questions if the underlying policies, permit conditions, or clinician responses are not captured in a structured, episode-level record.

Conventional integrations of intra-body robotic DSIs with imaging consoles, catheterization laboratory systems, endoscopy platforms, or EHR workflows often rely on vendor-specific audit logs that are not aligned to a common safety receipt schema and do not represent, in a machine-verifiable manner, the policies, permit decisions, and human-in-the-loop confirmations governing each robotic maneuver or therapeutic step. As a result, health systems, payers, and regulators may find it difficult to reconstruct which DSIs, configuration profiles, or control policies were active when an intra-body robot navigated to a target, delivered a therapeutic payload, or terminated a procedure, and whether those actions remained within intended indications, validation boundaries, and governance constraints.

Another class of high-consequence DSIs comprises therapy-planning and dose-titration decision support modules for advanced biologic and interventional therapies, such as gene therapies, cell therapies, programmable RNA-based therapeutics, and neuromodulation or implant programming procedures. Such DSIs may assist with selecting patients for a particular therapy, choosing targets or vectors, proposing initial or adaptive dosing regimens, or recommending changes to programmed stimulation parameters based at least in part on longitudinal laboratory, imaging, or symptom data. When deployed without a structured, episode-level safety receipt layer, these therapy-planning DSIs may materially influence initiation, continuation, or intensification of high-risk therapies without a canonical and machine-verifiable record of the policies, permit predicates, and human-in-the-loop confirmations that governed each recommendation.

Regulatory frameworks and certification programs for health IT increasingly require, among other things: (i) transparency regarding the data inputs and logic used by DSIs, (ii) disclosure of known limitations and appropriate use conditions, (iii) monitoring of DSI performance and bias over time, and (iv) retention of auditable records of DSI recommendations and clinician responses. However, many existing EHR implementations primarily treat these requirements as static documentation obligations (for example, model cards or configuration metadata) rather than as run-time execution guarantees that are enforced when each DSI is actually invoked.

Conventional audit logging features in EHR systems may record which user accessed which patient record at which time, and may capture some information about which clinical decision support alerts were displayed. But such logs are typically: (i) not structured to represent the full context of a DSI episode, (ii) not bound to explicit policy graphs describing when a DSI was permitted to act, (iii) not fail-closed (that is, DSIs may execute even if compliance checks fail or are skipped), and (iv) not encoded as machine-verifiable safety receipts that can be shared with payers, regulators, or external auditors while preserving patient privacy.

As a result, health systems, payers, and regulators may struggle to reconstruct exactly what an AI-assisted DSI did, under which policies, and how clinicians responded. This increases the risk of unsafe recommendations, inappropriate reliance on AI outputs, and post-hoc disputes about whether a given intervention complied with applicable safety, fairness, or use-conditions policies.

There is therefore a need for systems and methods that implement a safety receipt layer for AI-assisted DSIs, such that: (i) relevant clinical context is captured at the moment a DSI is invoked, (ii) a policy graph is evaluated to determine whether the DSI may proceed, must be modified, or must be blocked, (iii) DSI execution is gated by a permit-before-action mechanism, and (iv) a structured, tamper-evident safety receipt is emitted for each DSI episode, capable of being anchored into one or more audit stores and later verified by internal and external stakeholders.

Certain health IT transparency and certification frameworks further contemplate that developers and implementers of DSIs will collect and report aggregate usage and performance information, such as volumes of DSI use, override rates, alert burden, performance or calibration metrics stratified by population segment, and summaries of safety incidents. Without a structured, episode-level representation of each DSI execution that can be aggregated in a consistent and privacy-preserving manner, such monitoring and reporting obligations may be difficult to meet in practice and may rely on ad hoc logs or sampling that provide incomplete visibility into real-world DSI behavior. Multi-condition imaging DSIs, in particular, may require monitoring of case volumes, detection performance, and disparities across imaging indications or patient subpopulations, yet such monitoring is challenging without a consistent episode-level representation.

From a technical perspective, the safety receipt layer described herein can improve the functioning of the underlying clinical computing systems themselves. By interposing a permit-before-action gate within a DSI invocation path and requiring successful generation and anchoring of a structured safety receipt before a DSI output is finalized, the safety receipt layer enforces deterministic control-flow that is not achievable using conventional, post-hoc audit logging alone. For example, in some embodiments the safety receipt layer prevents inconsistent states in which a DSI output is displayed to a clinician without a corresponding, verifiable record of the inputs, policies, and permit outcome, and reduces the need for ad hoc reconstruction of disparate logs during audits or incident investigations. In certain implementations, the safety receipt layer further reduces redundant database queries and logging operations by canonicalizing clinical context into a reusable clinical context envelope, thereby improving memory and processor utilization compared to naive logging approaches that repeatedly materialize similar context for each DSI component.

From a computing-systems perspective, the HTI safety receipt layer operates as a middleware or platform component that enforces a deterministic permit-before-action invocation pattern between the EHR system and one or more DSI engines. By moving policy evaluation, safety receipt generation, and, in some embodiments, anchoring preconditions into the critical path of DSI invocation, the safety receipt layer eliminates classes of inconsistent states in which DSIs modify clinical workflows without a corresponding, verifiable record of the inputs, policies, and permit outcome. In various implementations, the safety receipt layer further reduces redundant database queries and logging operations by canonicalizing clinical context into a reusable clinical context envelope for multiple DSIs, thereby improving memory and processor utilization compared to naive logging approaches that re-materialize similar context for each DSI component while also strengthening safety and auditability guarantees. Accordingly, the HTI safety receipt layer constitutes a computer-implemented improvement to clinical computing infrastructure, because the described deterministic permit-before-action latch, canonicalization, and idempotent finalization mechanisms change how the EHR and DSI engines operate at runtime rather than merely documenting existing human policies.

From a revenue-cycle and coverage perspective, emerging reimbursement pathways for AI-enabled clinical services (including, for example, separate or add-on payments for certain AI-assisted imaging, diagnostic, or monitoring interventions) require that health systems be able to produce machine-verifiable, episode-level evidence showing when a given AI-assisted DSI was invoked, under which policies, and whether it remained within its intended indication and governance constraints. Conventional billing and audit logs are typically not structured to represent such evidence in a reusable, cryptographically anchored form and often cannot distinguish between episodes in which AI outputs materially influenced care and episodes in which the same technology was dormant or operating in a different mode. As a result, revenue-cycle computing systems may be unable to implement precise, automated integrity checks for AI-assisted services or to provide reliable, privacy-preserving evidence to payers and regulators for coverage determinations and audits.

There is therefore a further need for systems and methods that allow the same structured, tamper-evident safety receipts which gate DSI execution to be reused as machine-verifiable evidence objects for revenue-cycle integrity controls, coverage and reimbursement workflows, and payer or regulator audits, while preserving the separation between clinical permit-before-action gate predicates and downstream billing logic.

Emerging regulatory and payment pilots for digital health and AI-enabled chronic-disease technologies permit earlier or expanded clinical use under enforcement discretion or conditional coverage, provided that implementers collect and report structured real-world evidence (RWE) regarding safety, performance, and equity for enrolled patient cohorts. However, many conventional EHR and DSI integrations lack a standardized, episode-level, tamper-evident evidence object that can be reused across multiple oversight and payment programs, forcing implementers to rely on ad hoc data extracts and duplicated logging pipelines that are brittle, non-deterministic, and difficult to audit at scale.

In parallel, chronic-care and technology-enabled care models are shifting toward outcomes-based or population-based reimbursement arrangements, in which continued coverage or payment may depend on verifiable links between (i) how AI-assisted DSIs are invoked in day-to-day care and (ii) longitudinal clinical outcomes, safety incidents, and equity indicators for specific population segments. Without a runtime governance layer that deterministically binds each AI-assisted DSI episode to applicable policies, permit outcomes, and downstream revenue-cycle events, health systems may struggle to participate in such pilots or models while demonstrating that AI-enabled services remain within intended indications and governance constraints.

In some embodiments, the same structured, tamper-evident safety receipts that gate DSI execution may be reused as machine-verifiable evidence objects for technology-enabled chronic care, remote monitoring, and other value-based or outcome-aligned payment programs, where payers or regulators require episode-level proof that AI-assisted interventions were invoked, governed, and monitored in conformance with applicable policies. Such reimbursement or coverage uses are evidentiary overlays only and do not alter the permit-before-action semantics or fail-closed behavior enforced by the safety receipt layer; the claims control.

ACCESS-style chronic care payment models (illustrative; non-limiting). By way of example and not limitation, national or regional payers may implement outcomes-based chronic care payment models similar to ACCESS-style (Advancing Chronic Care with Effective, Scalable Solutions-style) programs in which recurring payments for technology-enabled hypertension, diabetes, heart failure, chronic obstructive pulmonary disease (COPD), depression, or other chronic-disease services depend on verifiable improvements in risk-adjusted outcomes for enrolled patient cohorts (such as changes in blood pressure, hemoglobin A1c, hospitalization rates, or exacerbation-free days for respiratory conditions) over defined observation windows. In such configurations, the same structured, tamper-evident safety receipts that gate AI-assisted decision support interventions at the DSI-episode level may be reused as canonical evidence objects showing when, how, and under which governance predicates AI-assisted chronic-care interventions were invoked for enrolled patients, without altering the underlying permit-before-action semantics or fail-closed behavior enforced by the safety receipt layer; the claims control.

In some embodiments, revenue-cycle or billing systems maintain explicit provenance or AI-use annotations for billing records, such that, by way of example and not limitation, a billing code, modifier, relative value unit (RVU), or other billing attribute is marked as AI-influenced when it was inserted, adjusted, or recommended by an AI-assisted coding engine, an AI-assisted DSI, or an AI-assisted summarization or documentation service. An AI-governed billing gate can treat such marked billing events as AI-influenced billing events when evaluating whether safety receipt preconditions are satisfied before submitting, auto-adjudicating, or finalizing the corresponding claim line. These classifications are for traceability and evidence routing only; clinical gate predicates remain exclusively within the safety receipt layer.

In such configurations, billing events may be classified into AI-governed billing events, for which safety receipt preconditions are enforced by an AI-governed billing gate, and non-AI or AI-ungoverned billing events, which may bypass or minimally engage the AI-governed billing gate while remaining subject to other applicable billing controls. This separation allows AI-influenced billing pathways to remain explicitly traceable to underlying safety receipts and governance predicates without requiring that all billing events be routed through the same safety receipt preconditions. These classifications are for traceability and evidence routing; clinical gate predicates remain exclusively within the safety receipt layer.

Motivation and ethical context (illustrative; non-limiting). The systems and methods described herein are motivated by a commitment to use advanced computing in service of loving and protecting patients and neighbors-particularly vulnerable patients-rather than as a source of opaque or unaccountable automation. The safety receipt layer is intended to help health systems deploy AI-assisted decision support in a way that strengthens safety, transparency, and fairness, so that AI is treated as a tool for care, stewardship, and accountability. This ethical motivation is provided for background context only and is not intended to limit or interpret the scope of the claimed invention; the claims and written description control. In some embodiments, this ethical motivation is implemented technically by enforcing a deterministic, permit-before-action safety layer at the EHR-DSI boundary that reduces race conditions, prevents inconsistent render and write-back states, and requires generation of a verifiable safety receipt for each DSI episode before the AI-assisted recommendation is rendered or any DSI-initiated write-back is committed.

V. SUMMARY

In various embodiments, the present disclosure provides systems and methods for HTI-ready safety receipt layers that sit between EHR systems and AI-assisted DSIs. In some embodiments, the safety receipt layer is configured to be HTI-ready for multiple classes of DSIs, including rules-based alerts, risk-score calculators, large language model (LLM)-based assistants, imaging-based triage or reporting models, AI-assisted intra-body robotic navigation and intervention systems, and therapy-planning DSIs for advanced biologic and interventional therapies (for example, gene or cell therapies, programmable RNA-based therapeutics, or neuromodulation and implant programming procedures), such that each invocation of a DSI yields a corresponding safety receipt.

In one embodiment, a system includes: an EHR system configured to provide patient data and user session metadata; a DSI engine configured to generate one or more AI-assisted clinical recommendations; a safety receipt layer including (i) a context capture module, (ii) a policy graph evaluation engine, (iii) a permit and override decision engine, and (iv) a safety receipt generator; and a tamper-evident anchor service. The safety receipt layer intercepts DSI requests, captures a clinical context envelope, evaluates a policy graph to determine whether the requested DSI execution satisfies applicable policies, and, when permitted, generates a safety receipt comprising structured fields describing at least the inputs, policies, permit outcome, and clinician response for the DSI episode.

In some embodiments, the safety receipt layer is configured such that, when policy evaluation fails, a permit condition is not satisfied, or a required safety receipt cannot be generated or anchored, the DSI behaves in a fail-closed manner: the AI-assisted clinical recommendation is blocked, downgraded, or replaced with a safer default pathway and is not delivered to any clinical workflow surface unless and until a permit condition is satisfied. In some embodiments, a structured failure-mode safety receipt is emitted for such episodes so that later reviewers can understand why the DSI output was blocked or downgraded under the applicable policies.

In some embodiments, safety receipts are encoded as proof-of-policy-compliance (PoPC) artifacts that can be stored locally within the EHR, remotely in a compliance registry, or anchored in a tamper-evident log or append-only audit store. Safety receipts may omit direct patient identifiers and instead include hashed or pseudonymous identifiers or linkable tokens, enabling external verification of DSI behavior and compliance while preserving protected health information (PHI).

In some embodiments, the safety receipt layer provides configuration surfaces that map specific DSI types (for example, sepsis alerts, dosage calculators, discharge-planning assistants, or multi-condition imaging triage models) to policy graph templates and safety receipt schemas. This arrangement enables enrollment of new DSIs or updates to existing DSIs to be performed primarily through configuration rather than code-level changes, facilitating consistent governance across multiple care settings, institutions, or vendor deployments.

In some embodiments, the safety receipt layer exposes one or more application programming interfaces (APIs) or module interfaces adapted for integration with health IT transparency or certification programs. These interfaces can include fields and mapping logic that associate safety receipt fields with documentation elements such as data inputs, intended use and limitations, risk mitigation strategies, monitoring indicators, and governance processes, thereby supporting preparation of required transparency or certification artifacts from runtime evidence.

In some embodiments, the safety receipt layer is configured such that safety receipts include optional regulatory metadata fields and profile identifiers that can be mapped to specific health IT transparency, certification, or AI-governance frameworks. For example, a given transparency or monitoring profile may correspond to a set of decision-support intervention transparency criteria issued by a national health IT coordinator, obligations for high-risk AI systems under jurisdictional AI legislation, or post-market monitoring guidance for adaptive machine-learning devices. Such regulatory mappings are evidence-only overlays that do not alter the permit-before-action semantics or fail-closed behavior enforced by the safety receipt layer; the claims control.

In some embodiments, the structured safety receipt schema further defines optional transparency_mapping and regulatory objects that associate receipt fields with DSI transparency elements and framework or profile identifiers for the corresponding clinical decision support intervention (DSI) engine. The transparency_mapping object may reference subject, context, policy, permit, monitoring, or extensions fields that satisfy particular transparency or documentation elements, while the regulatory object carries identifiers of DSI transparency profiles, framework profiles, and documentation hooks for health IT transparency, certification, or AI-governance programs. These overlays allow the same permit-before-action safety receipts to be interpreted both as execution-time records and as machine-readable evidence of conformance to one or more transparency frameworks, without changing the underlying permit-before-action or fail-closed semantics enforced by the safety receipt layer; the claims control.

In some embodiments, safety receipts generated under the disclosed permit-before-action semantics may further be aggregated or profiled to support participation in outcomes-based chronic care payment models (for example, national programs that condition recurring payments for technology-enabled chronic disease management on verifiable, risk-adjusted improvements in clinical outcomes for enrolled cohorts), while remaining evidentiary overlays that do not alter the core gate predicates or fail-closed behavior enforced by the safety receipt layer; the claims control.

In some embodiments, the regulatory object and related transparency mappings further encode optional profile identifiers and documentation hooks for outcomes-based chronic care and digital health pilots, including, by way of example and not limitation, outcomes-based chronic-disease payment models similar to ACCESS-style programs and real-world evidence pilots for digital health technologies similar to TEMPO-style initiatives. Such identifiers may include one or more framework_profile_ids or program-specific monitoring profile identifiers that bind safety receipts to corresponding chronic-care or real-world evidence monitoring postures for enrolled cohorts, while remaining evidentiary overlays that do not alter the permit-before-action semantics, fail-closed behavior, or core gate predicates enforced by the safety receipt layer; the claims control.

In some embodiments, the safety receipt additionally encodes a policy_digest and, when available, a policy_signature over a policy graph or policy profile, enabling external verifiers to confirm that the recorded permit outcome was computed under a specific, attested policy version.

In some embodiments, the safety receipt layer further includes an insights and monitoring module configured to aggregate safety receipts across multiple DSI episodes to compute usage, safety, and fairness metrics for one or more DSI types, care settings, and patient subpopulations. The insights and monitoring module may generate dashboards, reports, or machine-readable summaries describing, for example, frequency of DSI invocation, distributions of permit outcomes and overrides, alert burden, performance or calibration indicators stratified by protected or clinically relevant attributes, and summaries of safety incidents or near misses.

In some embodiments, the insights and monitoring module is implemented to consume safety receipts generated under the permit-before-action and fail-closed semantics of the safety receipt layer, such that aggregate metrics describing DSI usage, override behavior, alert burden, or performance and fairness indicators are derived from episodes that are known to have corresponding, verifiable receipts. This arrangement can help ensure that monitoring outputs and reports reflect actual executed DSI episodes, rather than inferred or partially sampled behavior, and can reduce discrepancies between runtime behavior and separately maintained documentation or model cards.

In some embodiments, the safety receipt layer is specifically configured to be HTI-ready for imaging-based DSIs, including chest-radiograph triage and reporting models, such that each invocation of an imaging DSI yields a corresponding safety receipt. In such embodiments, near-autonomous imaging behaviors-such as auto-normal triage labels or auto-generated chest-radiograph reports—can be operated under a tethered governance model in which permit-before-action semantics, override behavior, and accountability for imaging decisions remain observable at the episode level.

Various embodiments of the disclosure thus provide a runtime, policy-bound, and receipt-emitting safety layer for AI-assisted DSIs that improves the functioning of underlying clinical computing systems, helps health systems demonstrate compliance with evolving health IT governance expectations, reduces the risk of unsafe or unmonitored AI behavior, and supports efficient, evidence-based audits and incident investigations using structured, tamper-evident safety receipts.

VI. BRIEF DESCRIPTION OF THE DRAWINGS

VII. DETAILED DESCRIPTION

Figure 1:
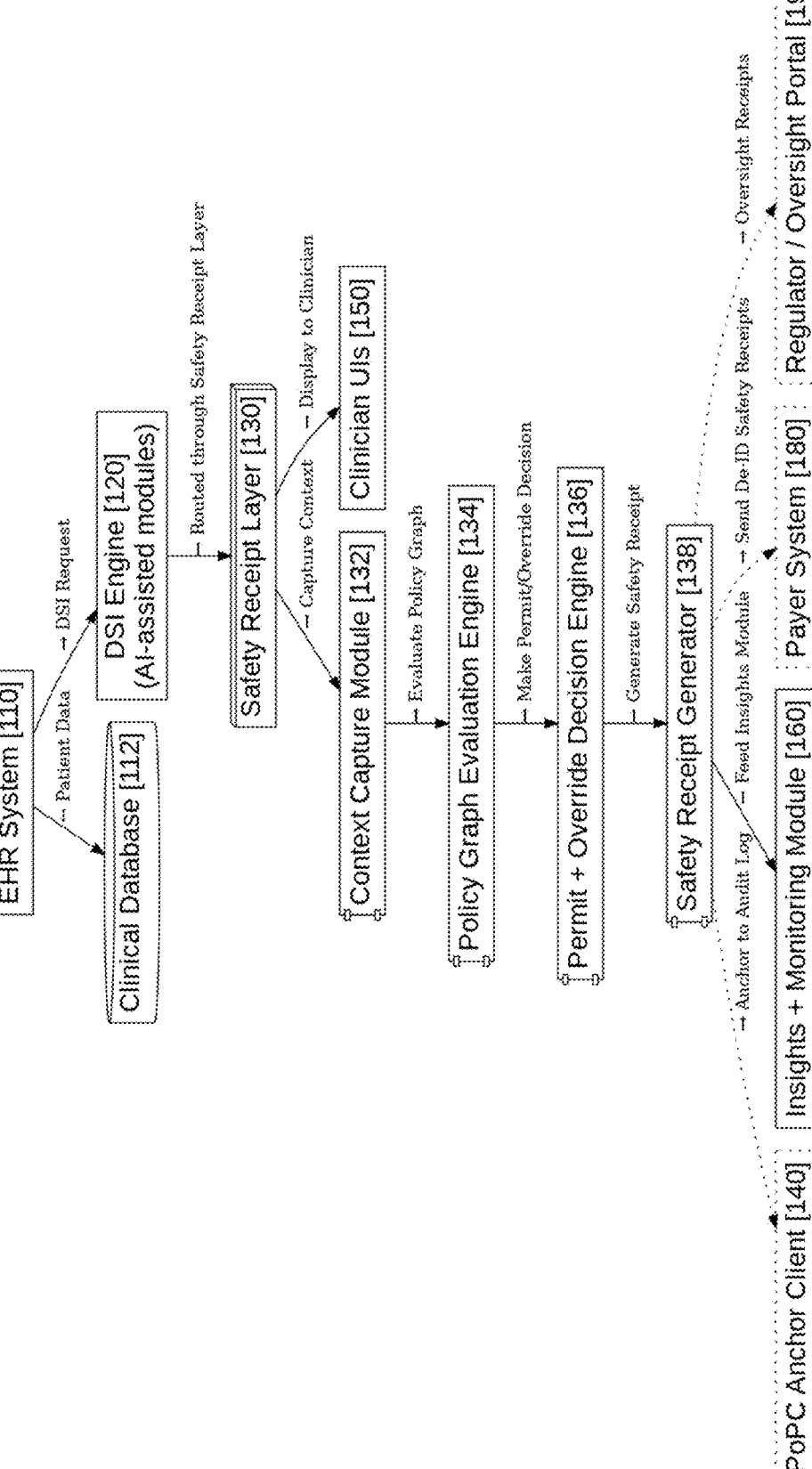
FIG. 1 is a block diagram of an illustrative clinical computing environment including an EHR system, one or more AI-assisted DSI engines, and an interposed safety receipt layer configured to gate DSI execution and emit structured safety receipts.

System Overview (FIG. 1)

FIG. 1 illustrates an example clinical computing environment 100. Environment 100 includes an EHR system 110 communicatively coupled to a clinical database 112, a DSI engine 120, a safety receipt layer 130, one or more clinician user interfaces (UIs) 150, an insights and monitoring module 160, and optionally one or more external systems such as a payer system 180 and a regulator or oversight portal 190.

EHR system 110 may include one or more modules for charting, order entry, medication management, and clinical documentation. Clinical database 112 may store structured and unstructured patient data such as vital signs, laboratory results, problem lists, medication lists, imaging reports, and clinical notes, as well as encounter and workflow metadata.

DSI engine 120 may include one or more AI-assisted modules such as a risk scoring model, an alerting module, a recommender system, or a conversational assistant. DSI engine 120 may be configured to receive a DSI request including patient identifiers or pseudonymous tokens, relevant context fields, and a requested DSI type. By way of example and not limitation, DSI engine 120 may include an imaging triage module configured to process radiology images, such as an abdomen-pelvis CT study, and to output one or more triage flags for multiple suspected urgent findings within the same study.

By way of another example, DSI engine 120 may include a chest-radiograph analyzer configured to process one or more chest x-ray images and to output triage flags, structured labels for suspected thoracic findings, or a draft radiology report or explanation that may be presented to a clinician or patient.

Safety receipt layer 130 is logically interposed between EHR system 110 and DSI engine 120 and includes a context capture module 132, a policy graph evaluation engine 134, a permit and override decision engine 136, and a safety receipt generator 138. In some embodiments, safety receipt layer 130 further includes a PoPC anchor client 140 configured to write safety receipts or references thereof to one or more tamper-evident audit stores, such as an append-only log or external compliance registry.

Clinician UIs 150 may be presented within EHR system 110 or in associated applications and may display DSI outputs, request additional input from clinicians, surface safety indicators or override options, and present summaries of safety receipts or policy context when requested.

Payer system 180 may request de-identified or pseudonymous safety receipts for episodes associated with high-cost or high-risk interventions, in order to verify that DSIs were used within intended indications and policy constraints. Regulator or oversight portal 190 may receive aggregate or case-specific safety receipts or summaries thereof for oversight, monitoring, or incident investigation purposes. In some embodiments, to minimize exposure of protected health information, pseudonymous identifiers for patients, encounters, sessions, or organizations are derived via a per-tenant keyed hash-based message authentication code (HMAC). In such configurations, the safety receipt may include an hmac_key_id or salt_id to support key rotation and linkage across receipts without enabling re-identification.

In some embodiments, environment 100 further includes a revenue-cycle governance rail or revenue-cycle management (RCM) truth rail 170 logically coupled to EHR system 110, safety receipt layer 130, and payer system 180. The revenue-cycle governance rail 170 is configured to generate structured revenue-cycle governance receipts or Revenue Cycle Truth Receipts that bind billed clinical events, procedure codes, payer or coverage identifiers, and, optionally, reimbursement modifiers to underlying clinical episodes and associated safety receipts. Safety receipt 400 may carry one or more cross-rail references to such revenue-cycle governance receipts, thereby allowing downstream revenue-cycle and payer systems to verify, in a machine-readable manner, that billed AI-assisted services were governed by appropriate policies and permit outcomes. Cross-rail references are evidentiary only and do not alter the internal policy-graph evaluation, permit-before-action semantics, or fail-closed behavior enforced by safety receipt layer 130; the claims control.

In some embodiments, revenue-cycle governance rail 170 and payer system 180 are further configured to participate in regulatory pilots or outcomes-based payment models for technology-enabled chronic-disease services, in which eligibility for, or continued participation in, a program depends on availability of real-world evidence derived from safety receipts over a defined cohort of DSI episodes. Safety receipts generated by safety receipt layer 130 provide the canonical, episode-level evidence objects that can be aggregated into program-specific evidence bundles without modifying the underlying EHR system or DSI engines.

By way of example and not limitation, a cardio-renal-metabolic (CRM) chronic-disease management DSI or a musculoskeletal rehabilitation DSI may be enrolled into a technology-enabled care program under which early deployment or enhanced coverage is conditioned on periodic submission of de-identified aggregates of safety receipts demonstrating adherence to governance predicates, permit outcomes, override behavior, and safety incident rates for enrolled population segments. These program-specific evidence bundles are derived from the same structured safety receipts that gate DSI execution on a permit-before-action and fail-closed basis, and program references are evidentiary overlays that do not alter gate predicates; the claims control.

By way of example and not limitation, a payer or national health program implementing an outcomes-based chronic care model similar to an ACCESS (Advancing Chronic Care with Effective, Scalable Solutions)-style payment program may treat de-identified aggregates of safety receipts for enrolled chronic-disease decision support interventions as canonical evidence bundles for verifying that AI-assisted services were invoked and governed in accordance with applicable policies and governance predicates, without changing the permit-before-action or fail-closed semantics enforced by the safety receipt layer.

Insights and monitoring module 160 is configured to ingest safety receipts generated by safety receipt layer 130 and to compute aggregate metrics describing DSI usage and behavior. By way of example and not limitation, insights and monitoring module 160 may compute one or more of: (i) counts and rates of DSI invocations by DSI type, care setting, or clinician role; (ii) distributions of permit outcomes, including frequencies of permit, permit with guardrails, require override, and deny outcomes; (iii) override rates and distributions of override reason codes; (iv) incident flags or adverse event indicators associated with particular DSI episodes; and (v) performance or calibration metrics, such as sensitivity, specificity, or calibration error, evaluated on subsets of DSI episodes belonging to different patient subpopulations. Outputs of insights and monitoring module 160 may be surfaced to health system quality and safety teams, DSI developers, and regulators or oversight bodies in the form of dashboards, machine-readable reports, or alerts indicating anomalous patterns.

In some embodiments, insights and monitoring module 160, configuration console 604, or another transparency service maintains a registry of DSI transparency profiles for enrolled DSI engines or deployments. Each DSI transparency profile may include transparency attributes such as a DSI family or version identifier, a transparency profile identifier, plain-language intent or indication references, documentation references (for example, to developer model cards, risk-management plans, or post-market monitoring plans), and identifiers of applicable health IT transparency or AI-governance frameworks. At runtime, when safety receipt layer 130 generates safety receipt 400 for a DSI episode, the safety receipt generator may record, in the structured safety receipt, at least one identifier of the DSI transparency profile that was in effect (for example, an HTI profile identifier or framework profile identifier), thereby binding the DSI episode to a corresponding transparency posture and enabling aggregate analytics and oversight keyed by transparency profile while preserving patient privacy. Such identifiers may be encoded in transparency_mapping or regulatory objects of the receipt serialization, which remain evidentiary overlays that do not alter the permit-before-action or fail-closed semantics enforced by the safety receipt layer.

In some embodiments, insights and monitoring module 160 further exposes program-specific monitoring views and machine-readable interfaces tailored to regulatory pilots and outcomes-based payment models for chronic-disease DSIs. Such monitoring views may, by way of example and not limitation, summarize distributions of permit outcomes, override behavior, alert burden, and incident flags for cohorts enrolled in a technology-enabled chronic care program, together with population-segment stratifications derived from safety receipts. Program interfaces may allow external regulatory, coverage, or payment systems to retrieve pre-defined aggregates or evidence bundles derived from safety receipts under a specified monitoring profile, without requiring direct access to underlying patient identifiers or raw EHR data. In some embodiments, the monitoring interface supports keyed requests by DSI family, DSI type, care setting, population segment, monitoring-profile identifier, and aggregation window.

In some embodiments, an insights and monitoring module further generates machine-readable evidence bundles keyed by monitoring-profile identifiers and aggregation windows. Each evidence bundle can summarize metrics such as alert burden, override rates, performance stratified by population segments, or safety incidents, and can carry references to underlying safety receipts without exposing raw protected health information. Such evidence bundles are evidentiary only and do not alter permit-before-action or fail-closed predicates enforced by the safety receipt layer.

In some embodiments, the insights and monitoring module may also compute per-patient or per-family summary indicators derived from safety receipts, including counts of AI-assisted DSI episodes over a time window, proportions of episodes with overridden recommendations, proportions of episodes gated under fail-closed semantics, and counts of AI-related concerns or appeals submitted by or on behalf of a patient or family.

In some deployments, the system further supports generation of patient- or proxy-downloadable evidence packages for a specified DSI episode or case bundle, each evidence package comprising at least a human-readable summary of the episode or case, a machine-readable representation of the associated safety receipt or receipts, and a description of the rights exercised or available to the patient or proxy with respect to the episode or case.

In some embodiments, when one or more per-patient or per-family summary indicators exceed configured thresholds, the system may trigger escalation actions, such as temporarily downgrading AI-assisted DSI behavior to decision-support mode for the patient, requiring additional human review, or notifying a designated oversight or safety body.

Figure 2:
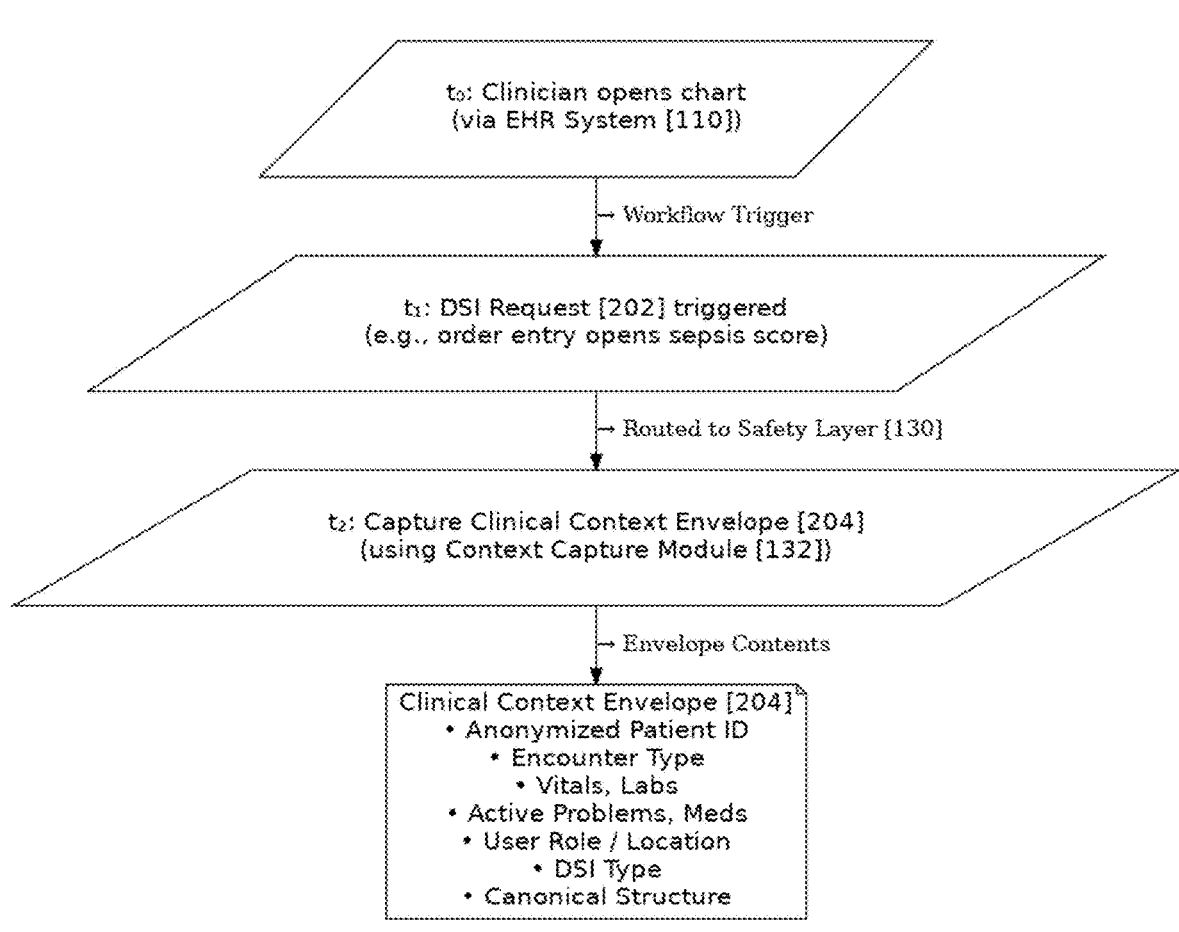
FIG. 2 is a timeline diagram of an illustrative DSI episode showing context capture, policy graph evaluation, permit and override decisions, DSI execution or blocking, clinician response, and emission of a corresponding safety receipt.
Figure 3:
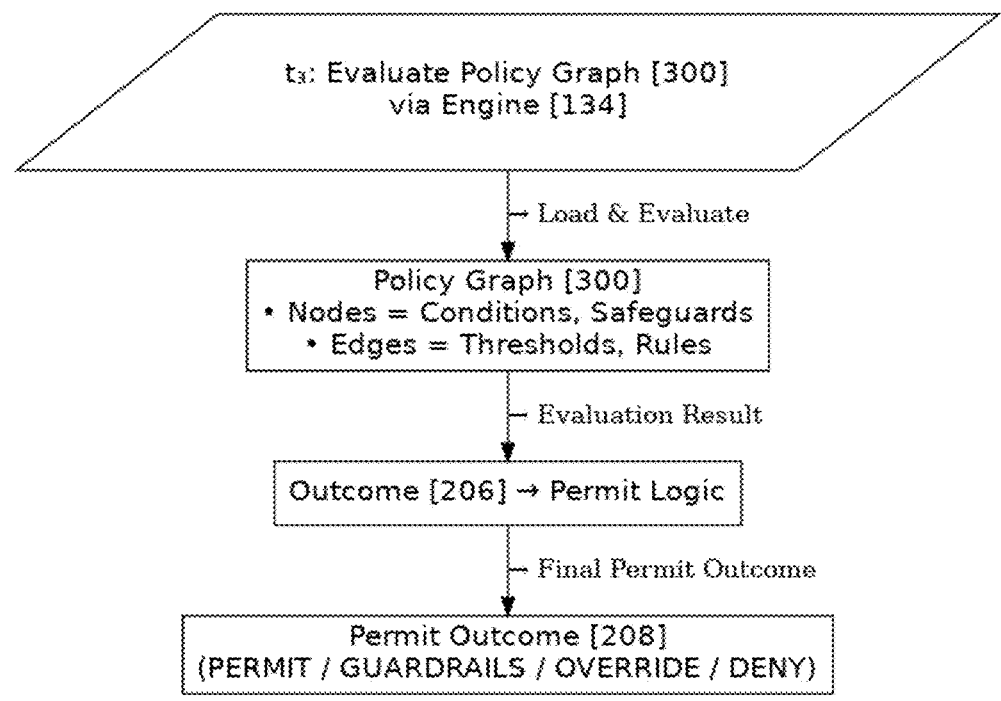
FIG. 3 is a conceptual diagram of an illustrative policy graph evaluated by the safety receipt layer to determine whether a requested DSI action is permitted, permitted with guardrails, requires override, or denied.

Context Capture and Policy Evaluation (FIGS. 2-3)

FIG. 2 illustrates an example DSI episode timeline 200. At time t0, a clinician opens a patient chart via EHR system 110. At time t1, clinician workflow triggers a DSI request 202 (for example, opening an order entry screen that invokes a sepsis risk score). At time t2, safety receipt layer 130 captures a clinical context envelope 204 using context capture module 132.

The clinical context envelope 204 may include, without limitation: an anonymized or pseudonymous patient identifier; encounter type (for example, inpatient, outpatient, emergency); relevant vital signs; recent laboratory results; active problems and medications; user role and permissions; device or location metadata; and a DSI type identifier. In some embodiments, the clinical context envelope 204 is represented in a canonicalized structure that can be reused across multiple DSI types or vendors.

FIG. 3 illustrates an example policy graph 300. At time t3, policy graph evaluation engine 134 evaluates a policy graph 300 (FIG. 3). Policy graph 300 may encode nodes and edges representing conditions, thresholds, safeguards, and routing rules determining whether DSI execution is permitted, requires modification, or must be blocked. For example, a policy graph may require that certain baseline data be present, that the DSI is not used for excluded subpopulations, or that certain safeguards (for example, conspicuous labeling or secondary confirmation) are active before allowing a given recommendation to be shown.

In some embodiments, policy graph 300 is versioned, and safety receipt 400 includes a policy graph identifier and version such that, at a later time, an auditor may reconstruct which policy logic was in effect for a given DSI episode. Policy graph versions may be updated over time in response to emerging evidence, regulatory guidance, or local governance decisions, while preserving the ability to interpret historical safety receipts under the policy regime that was active when the corresponding DSI episodes occurred.

Based on the outcome 206 of policy graph evaluation, permit and override decision engine 136 may compute a permit outcome 208. Outcomes may include, without limitation: PERMIT (normal DSI execution), PERMIT_WITH-_GUARDRAILS (for example, reduced capability or additional warnings), REQUIRE_OVERRIDE (explicit clinician attestation before proceeding), or DENY (block DSI execution). For an imaging triage DSI, a PERMIT WITH GUARDRAILS outcome may, for example, permit the triage model to generate triage flags while requiring that certain high-risk flags be accompanied by conspicuous labeling or secondary review by a radiologist before changing a worklist priority.

For chest-radiograph DSIs, a policy graph may, for example, distinguish between fully autonomous imaging behaviors-such as automatically marking a study as having no actionable finding or automatically finalizing a draft chest-radiograph report- and decision-support behaviors in which the same DSI outputs are presented as suggestions or highlights subject to mandatory human review. In some embodiments, policy graph evaluation engine 134 computes a permit outcome for the requested imaging behavior itself, such that autonomous imaging modes are permitted, permitted with guardrails, require explicit override, or are denied based at least in part on site-local validation metrics, monitoring indicators, or governance predicates encoded in the policy graph.

In some embodiments, permit and override decision engine 136 is integrated into the DSI invocation path in a fail-closed configuration, such that DSI engine 120 cannot produce or deliver an output to a clinician unless safety receipt layer 130 issues a positive permit or an explicitly logged override decision satisfying a permit condition. In some embodiments, the same fail-closed configuration further prevents any DSI-initiated write-back of orders or documentation to EHR system 110 for the DSI episode unless the permit outcome satisfies a permit condition, thereby avoiding states in which the DSI modifies the patient record without a corresponding safety receipt. In some embodiments, the gate enforces an atomic write barrier with an idempotency_token so that either both the permit record and the corresponding render or write-back finalize, or neither, preventing split-brain or duplicate finalizations across retries.

In some embodiments, the idempotency mechanism used to enforce atomic render and write-back finalization may be implemented not only via an explicit idempotency token, but also via other control primitives such as transaction fences, compare-and-swap-based commit markers, write-ahead-log (WAL) barriers, or functionally equivalent control mechanisms that prevent duplicate or split-brain finalizations across retries in distributed clinical computing environments.

In some embodiments, safety receipt layer 130 is deployed together with a trusted sensor ingress rail configured to validate imaging or other sensor acquisitions under a freshness policy and to emit per-event or per-study sensor receipts. For example, a medical-imaging ingress gateway may canonicalize a CT, MRI, or ultrasound study into one or more sensor receipts (sometimes referred to as S2 objects) anchored to a signed head of an append-only log under a freshness policy. In such embodiments, safety receipt generator 138 may include, in safety receipt 400, one or more references to such sensor receipts and, optionally, a profile identifier describing the sensor-ingress posture for the underlying data source. These references provide audit- and observability-only links in a chain of custody from capture to decision support and do not alter the permit-before-action semantics or fail-closed behavior of safety receipt layer 130.

In further embodiments, when outputs of DSI engine 120 are rendered as overlays on imaging studies or other clinical views controlled by an operating-system compositor, a trusted reality compositor (for example, a Trusted Reality Compositor (TRC) module that validates per-overlay Reality Receipts (R2) under a freshness and anti-replay policy) may gate rendering of those overlays. In such configurations, the compositor applies its own view-permit latch at the pixel path, and safety receipt 400 may include optional fields referencing one or more Reality Receipts associated with downstream visualization of the DSI episode. These references are evidentiary only and do not alter the permit-before-action semantics or fail-closed behavior of safety receipt layer 130.

In a representative imaging configuration, an abdomen-pelvis CT study is acquired through a trusted sensor ingress gateway (for example, a TSIL-Scan medical-imaging ingress gateway) that generates a per-series or per-frame Sensor Receipt (S2 or S2-MED) for the study and anchors it under a freshness policy; an imaging triage DSI as described above evaluates the study under a policy graph enforced by safety receipt layer 130 and emits a safety receipt 400 describing the DSI episode; and a reality compositor renders AI-assisted annotations or triage indicators only when accompanied by a validated reality receipt satisfying compositor policies. In such a multi-rail stack, optional cross-rail references among the sensor receipts, safety receipt 400, and any reality receipts provide an end-to-end, chain-of-custody record from capture through AI-assisted decision support and visualization without changing the internal gate semantics of any individual rail.

By way of another example, an AI-enabled cardiac analysis service deployed in a hospital-associated outpatient clinic or imaging center may be invoked as a DSI that processes one or more sensor waveforms or imaging studies acquired from a patient. Safety receipt layer 130 can gate this outpatient DSI under a policy graph that encodes site-local validation and oversight predicates, emit a corresponding safety receipt 400, and, optionally, allow revenue-cycle governance rail 170 and payer system 180 to use cross-rail references to the safety receipt when adjudicating reimbursement for the associated outpatient encounter. This arrangement allows outpatient AI-enabled services, including services billed under specific device, procedure, or technology-add-on codes, to be operated under the same permit-before-action and fail-closed semantics as inpatient DSIs, while providing machine-verifiable evidence suitable for coverage, auditing, and quality-improvement programs.

In some embodiments, safety receipts generated by safety receipt layer 130 are further consumed by a Safety Risk Budget Engine, which aggregates safety signals across multiple DSI episodes into a multi-harm risk vector and emits Safety Evidence Receipts for AI-assisted clinical episodes. Cross-rail references between HTI safety receipts and Safety Evidence Receipts are evidentiary only and do not alter the permit-before-action semantics or fail-closed behavior enforced by safety receipt layer 130.

In some embodiments, safety receipt layer 130 is used in multimodal and LLM-assisted radiology workflows. For example, an LLM-based report assistant or explainer may consume one or more imaging studies, prior report text, and structured clinical context to draft a radiology report or a patient-facing explanation. For each such DSI episode, safety receipt 400 may record a model identifier and version, a summary of prompts or retrieved context used to generate the draft, and, optionally, references to one or more guideline or protocol identifiers consulted by the model. These fields are evidentiary only; permit-before-action semantics and fail-closed behavior of safety receipt layer 130 remain governed by safety predicates over the DSI episode and its policy graph evaluation outcome.

In some embodiments, safety receipt layer 130 governs not only single-invocation decision support interventions but also multi-step or agentic clinical workflows in which one or more autonomous or semi-autonomous agents orchestrate a sequence of DSIs, retrieval operations, or documentation steps. Each such agentic workflow can be treated as a bounded DSI episode or as a hierarchy of sub-episodes, all of which are subject to the same permit-before-action and fail-closed semantics described herein, and each step or sub-episode can be associated with a corresponding safety receipt or cross-referenced in a parent safety receipt.

Treating agentic clinical workflows as bounded episodes or hierarchies of sub-episodes under a common safety receipt schema allows the same permit-before-action and fail-closed semantics to be applied to complex, multi-step AI behaviors without modifying the underlying EHR system or DSI engines. Instead of relying on bespoke orchestration logs or ad hoc instrumentation, the safety receipt layer enforces a uniform control structure in which each step is gated by a permit outcome and reflected in a structured safety receipt, thereby simplifying audits, reducing the risk of ungoverned agentic behaviors in production environments, and improving the determinism and observability of clinical computing systems that host such workflows.

In some embodiments, safety receipt layer 130 is configured to gate so-called autonomous imaging modes in which an imaging DSI proposes to auto-complete one or more clinical actions, such as committing a "no actionable finding" label for a chest radiograph, auto-finalizing a draft chest-radiograph report, or triggering a downstream care-pathway recommendation without mandatory human signoff for every episode. In such embodiments, policy graph evaluation engine 134 evaluates safety and governance predicates specific to the autonomous imaging behavior, including, for example, whether site-local performance metrics for a relevant risk stratum remain within configured bounds, whether required monitoring or incident-review programs are active, and whether applicable institutional or regulatory policies permit autonomous operation for the DSI type. When these predicates are not satisfied, permit decision engine 136 may allow the same DSI to operate in a decision-support-only mode while denying or suspending the autonomous imaging mode, and safety receipt 400 encodes both the mode requested and the mode actually permitted for the DSI episode.

Figure 4:
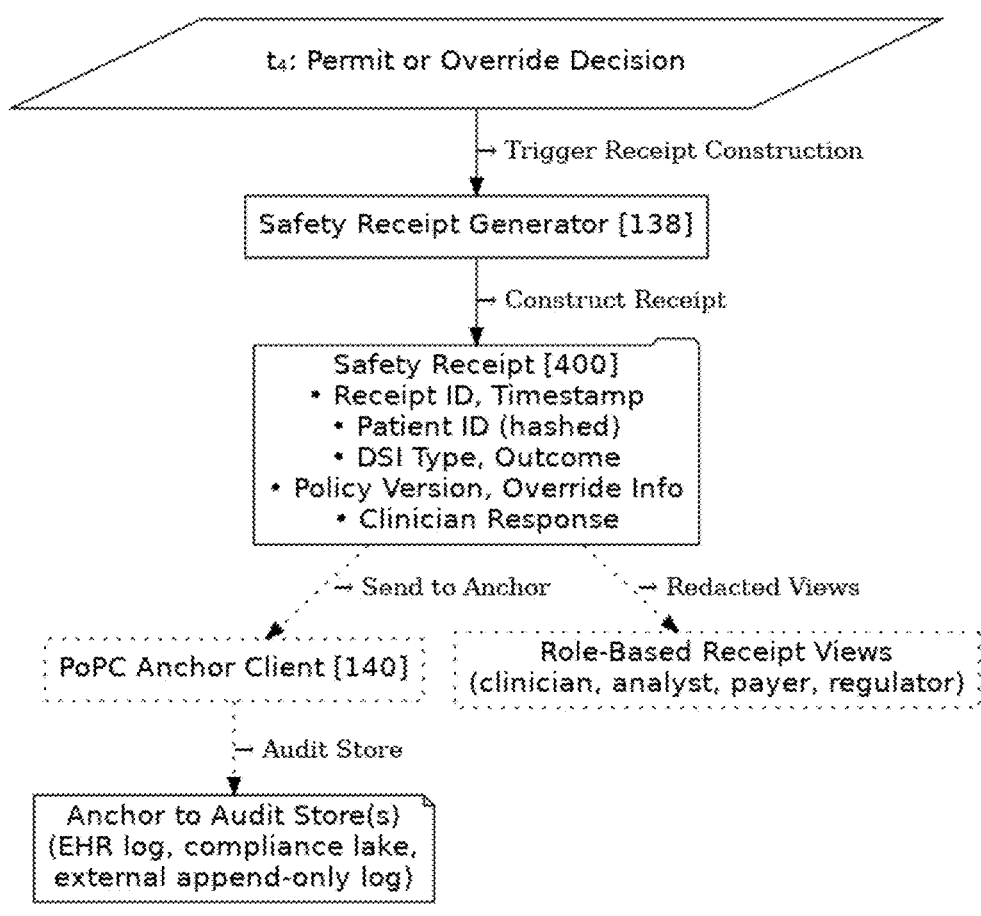
FIG. 4 is a schematic representation of an illustrative safety receipt schema, including structured fields suitable for representing DSI inputs, policies, permit outcomes, and clinician responses and for mapping to health IT transparency or certification requirements.

Safety Receipt Generation and Anchoring (FIG. 4)

FIG. 4 illustrates an example safety receipt 400 for a DSI episode. At time t4, when a permit or override outcome is determined, safety receipt generator 138 constructs safety receipt 400. Safety receipt 400 may include fields such as:

a receipt identifier; timestamp(s); DSI type identifier; hashed or pseudonymous patient identifier; context summary; policy graph identifier and version; policy evaluation outcome; any override type and reason codes; DSI output summary; and clinician response (for example, accepted, partially accepted, ignored, or contradicted by subsequent orders or documentation).

Safety receipts may be encoded using a structured serialization format (for example, JSON, XML, or protocol buffers) and may include cryptographic integrity protections, such as a digital signature or message authentication code computed by or on behalf of safety receipt layer 130.

In some embodiments, safety receipt generator 138 further encodes, in safety receipt 400, (i) an explicit listing of electronic health record (EHR) fields and clinical decision support intervention (DSI) metadata fields that were included in clinical context envelope 204 and (ii) a cryptographic digest of that listing, for example a cryptographic hash computed over a canonicalized representation of the field paths and values. This explicit listing and digest provide a machine-verifiable binding between the permit outcome recorded in safety receipt 400 and the clinical context envelope from which that outcome was computed.

In some embodiments, safety receipt layer 130 further exposes a verification interface that, when provided with EHR and DSI logs for a given DSI episode, reconstructs the corresponding clinical context envelope, recomputes the listing of context fields and the digest, and compares the recomputed digest to the cryptographic digest stored in safety receipt 400. A successful match confirms that the permit outcome recorded in the safety receipt was generated from that clinical context envelope, whereas a mismatch may trigger a fail-closed behavior for subsequent DSI invocations, a safety review, or a governance alert; underlying permit-before-action and fail-closed semantics remain governed by the policy-graph evaluation and gate predicates described herein. The canonicalization used for recomputing the cryptographic digest applies stable field ordering, type normalization, locale-invariant numeric formatting, timezone-normalized timestamps, and stable encodings for null and empty values to ensure reproducible verification across implementations.

In some embodiments, the safety receipt payload is signed (receipt_signature) under a rotating key (key_id), enabling end-to-end tamper detection prior to anchoring.

PoPC anchor client 140 may transmit safety receipt 400 or a derived digest thereof to one or more audit stores, such as an internal EHR audit table, a hospital compliance data lake, or an external tamper-evident logging service. Anchoring may occur synchronously or asynchronously, but in some embodiments, a minimal anchoring precondition must be satisfied before finalizing the DSI output to the clinician.

In some embodiments, the tamper-evident audit store is implemented as an append-only verifiable log that publishes signed heads under a maximum-merge-delay (MMD) freshness policy and provides inclusion proofs for appended entries and consistency proofs upon head advance. The anchoring precondition is satisfied only upon verification of an inclusion proof against a fresh signed head.

In some embodiments, if the PoPC anchor client 140 cannot obtain, within a configured maximum-merge-delay interval, an inclusion proof showing that safety receipt 400 or its derived cryptographic digest is included under a fresh signed head of the append-only verifiable log, the safety receipt layer treats the anchoring precondition as unsatisfied, transitions the DSI episode to a deny or failure path under fail-closed semantics, and emits a failure-mode safety receipt with a reason code indicating an anchoring-related condition, such as ANCHOR STALE or ANCHOR UNAVAILABLE.

In some embodiments, the PoPC anchor client 140 further records, in safety receipt 400, a status tuple comprising at least a signed_head_id, a head_timestamp, and a staleness-_interval derived from the anchoring event and an applicable maximum-merge-delay freshness policy. This status stapling enables downstream verifiers to reassess the freshness of the anchoring event against an applicable maximum-merge-delay policy at review time.

In some embodiments, a permit carries a validity interval (permit_validity_ms). If the interval elapses, or if a permit is revoked via a revocation_id recorded by an anchor or governance service, the safety receipt layer treats the permit condition as unsatisfied, transitions the DSI episode to a deny or failure path under fail-closed semantics, and emits a failure-mode safety receipt with a reason code such as PERMIT EXPIRED or PERMIT REVOKED.

Safety receipts may be retrievable by authorized parties for subsequent analysis. For example, payer system 180 may request a bundle of safety receipts for a cohort of episodes meeting predetermined billing codes, or regulator or oversight portal 190 may receive aggregate statistics on DSI usage, overrides, and failure modes derived from safety receipts.

In some deployments, revenue-cycle governance rail 170 or payer system 180 is further configured to treat the presence of a valid, anchored safety receipt or safety-receipt identifier as a precondition for submitting, finalizing, or paying particular classes of claims associated with AI-assisted DSIs. For example, a claim line corresponding to an AI-assisted imaging triage service or other AI-enabled diagnostic service may be submitted or auto-adjudicated only if a referenced safety receipt 400 indicates that the underlying DSI episode was permitted under an applicable policy profile and operated within its intended indication. By integrating safety receipt identifiers and anchoring proofs into revenue-cycle workflows in this way, the disclosed systems can prevent inconsistent computational states in which AI-assisted DSIs materially influence clinical and billing decisions without a corresponding, verifiable safety record, thereby improving the functioning of both clinical and revenue-cycle computing systems while preserving the separation between clinical gate predicates and billing logic. In some deployments, permit-before-bill semantics are enforced on both internal charge-capture events and outbound claim messages prior to auto-adjudication or payment.

In some deployments, when a safety receipt precondition is not satisfied for an AI-influenced billing event, the billing or revenue-cycle system may route the corresponding claim line to a manual review queue and mark it with an AI non-compliance indicator, thereby preventing auto-adjudication until the compliance issue is resolved.

In some embodiments, safety receipt layer 130 and insights and monitoring module 160 are further configured to support role-based receipt views, in which different actors receive differently redacted or transformed representations of a safety receipt. For example, a treating clinician may be permitted to view a near-complete representation of a safety receipt for a DSI episode involving the clinician's own patient; a hospital quality or compliance analyst may be permitted to view pseudonymized or aggregated safety receipts for cohorts of episodes; payer system 180 may receive de-identified receipts or aggregates thereof limited to fields relevant to coverage policies; and regulator or oversight portal 190 may receive further redacted or aggregated summaries sufficient to evaluate DSI safety, performance, and equity without exposing direct identifiers. Role-based receipt views may be governed by one or more role and policy configurations stored by safety receipt layer 130.

In some deployments, the safety receipt layer may further support patient- or caregiver-facing receipt views or explanations derived from safety receipts, for example by exposing redacted, plain-language summaries of why a particular AI-assisted recommendation was made, under which safeguards, and with what role for human oversight, while preserving privacy and without altering the underlying permit-before-action or fail-closed gate semantics.

In some embodiments, role-based receipt views and patient- or caregiver-facing views are rendered as redacted or transformed representations of a canonical safety receipt, such that the underlying permit outcome, policy identifiers, and anchoring evidence remain unchanged. These derivative views do not alter the safety receipt layer's policy-graph evaluation, permit-before-action semantics, or fail-closed behavior; instead, they provide tailored transparency and oversight surfaces for different actors while preserving a single, authoritative execution record for each DSI episode.

In some embodiments, the safety receipt layer maintains patient- or proxy-registered preference entries keyed by indication, DSI type, or DSI family, and recorded preferences are evaluated as additional gating predicates for subsequent DSI episodes while preserving the permit-before-action and fail-closed semantics described herein.

In some deployments, a patient- or proxy-initiated appeal generates a case bundle that references one or more safety receipts and, when applicable, associated revenue-cycle governance receipts, and exposes a review status under role-based access controls, without altering the underlying policy-graph evaluation, permit-before-action semantics, or fail-closed gate predicates enforced by the safety receipt layer.

In some deployments, patient- or caregiver-facing receipt views and explanations may be rendered in multiple languages and at different reading levels, and the safety receipt layer and associated patient truth interfaces may select an output representation for a given patient or caregiver based at least in part on stored language preferences, reading-level preferences, or assistive-technology indicators.

In some embodiments, role- and relationship-based views further distinguish adult patients, parents or legal guardians for minor patients, and time-bounded proxies, such that an adult patient may view explanation records for the adult patient, a parent or legal guardian may view explanation records for a minor patient for whom the parent or legal guardian is recorded as a guardian of record, and a designated proxy may be granted time-limited access to a subset of explanation records and case statuses for a specified patient, in each case without exposing safety receipt fields that identify other patients.

In some embodiments, when a patient or proxy exercises a truth or rights action with respect to a DSI episode, the system may emit a corresponding rights receipt that references an underlying safety receipt identifier and encodes the exercised right, a timestamp, an actor role, and a disposition, and may anchor such rights receipts in the same tamper-evident audit store used for safety receipts.

In some embodiments, creation or modification of patient- or proxy-registered preference entries may generate corresponding audit records that capture previous and new values, an actor role, and a timestamp, and that may be associated with subsequent safety receipts for DSI episodes governed by the preference entries.

Figure 5:
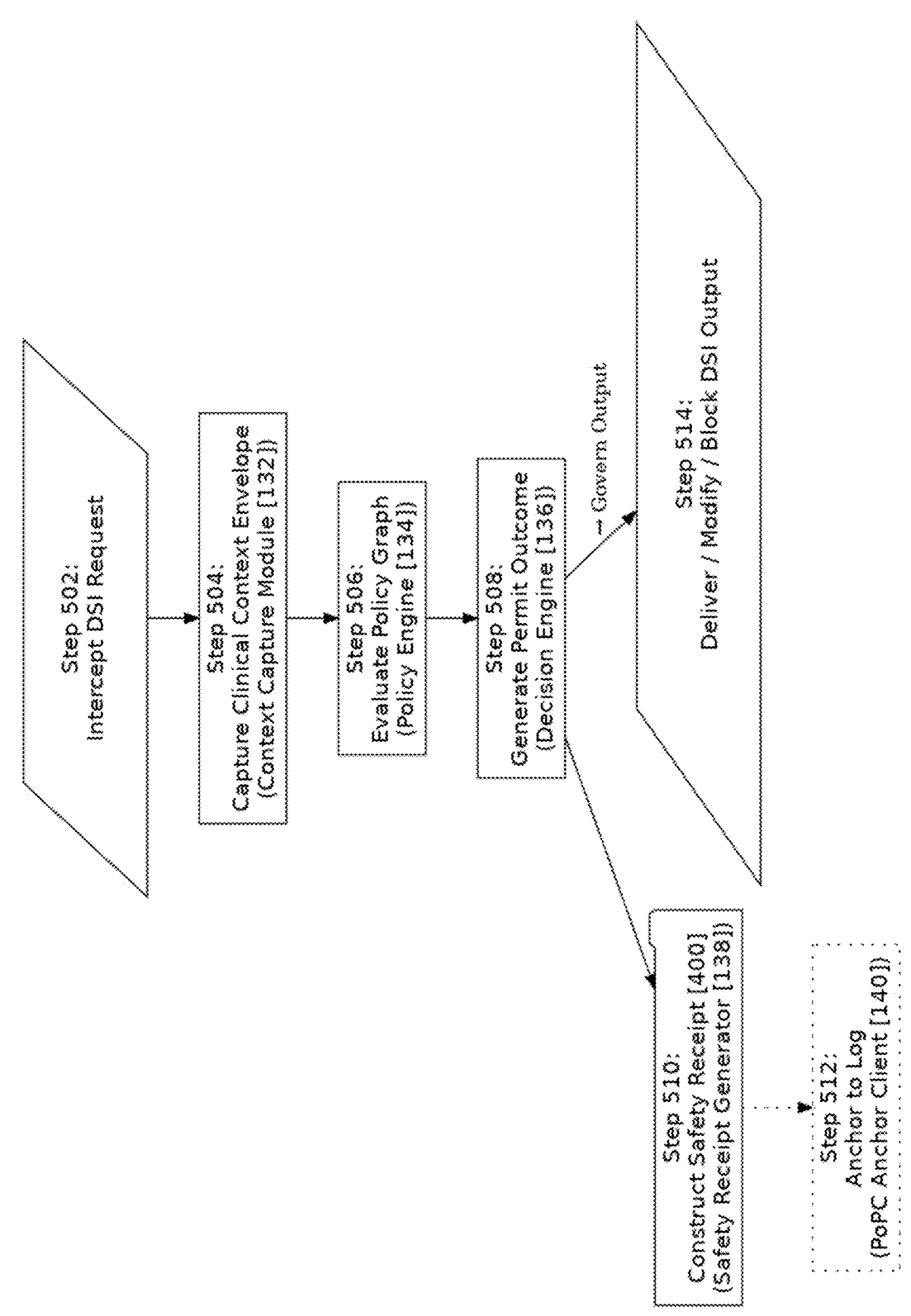
FIG. 5 is a flowchart of an illustrative method for generating a safety receipt for a DSI episode, including capturing a clinical context envelope, evaluating a policy graph, enforcing permit-before-action semantics, and anchoring the resulting safety receipt.
Figure 6:
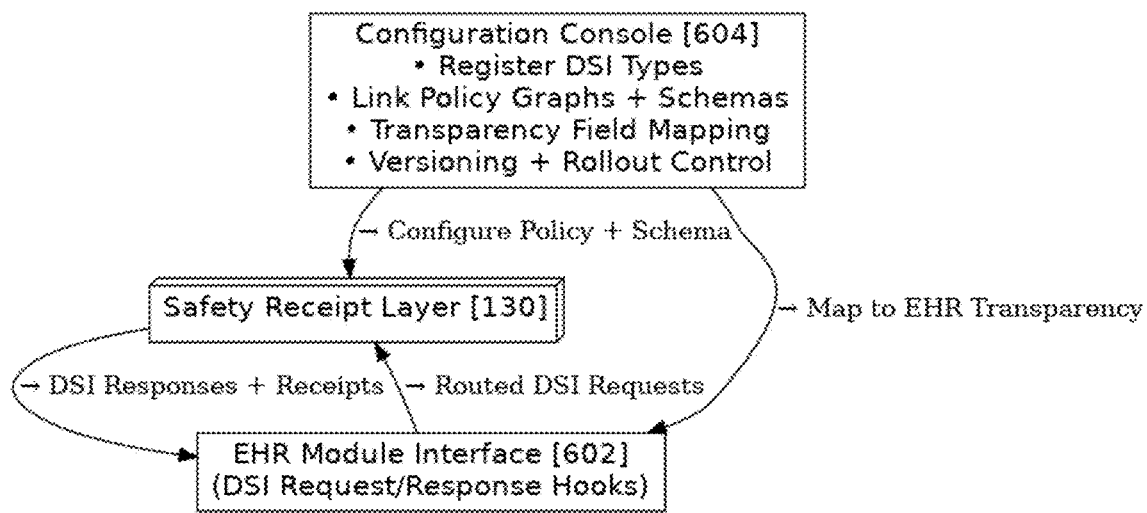
FIG. 6 is a block diagram illustrating integration of the safety receipt layer with one or more EHR module interfaces and a configuration console through which DSI types can be mapped to policy graph templates and safety receipt schemas.
Figure 7:
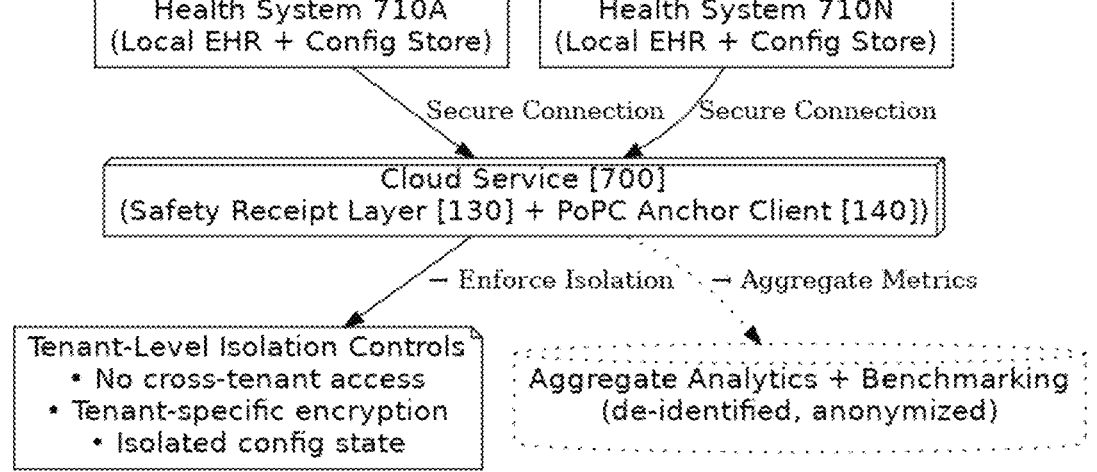
FIG. 7 is a diagram of an illustrative multi-tenant deployment of the safety receipt layer as a cloud service supporting multiple health systems or tenants while maintaining tenant-specific policies and audit stores.

Configuration and Health IT Integration (FIGS. 5-7)

FIG. 5 illustrates a method 500 implemented by safety receipt layer 130. At step 502, a DSI request is intercepted. At step 504, context capture module 132 constructs a clinical context envelope. At step 506, policy graph evaluation engine 134 evaluates applicable policies. At step 508, permit and override decision engine 136 generates a permit outcome. At step 510, safety receipt generator 138 constructs a safety receipt encoding context, policies, and outcomes. At step 512, PoPC anchor client 140 anchors the safety receipt or a digest thereof. At step 514, the DSI output is delivered, modified, or blocked according to the permit outcome.

FIG. 6 illustrates integration of safety receipt layer 130 with an EHR module interface 602 and a configuration console 604. EHR module interface 602 provides standardized hooks for DSI requests and responses. Configuration console 604 allows administrators to register DSI types, associate each type with a policy graph template and safety receipt schema, and map safety receipt fields to specific elements in a health IT transparency or certification framework. In some embodiments, configuration console 604 further supports versioning and rollout controls for updated policy graphs and receipt schemas.

FIG. 7 illustrates a multi-tenant deployment of safety receipt layer 130 as a cloud service 700. Multiple health systems 710A-710N may connect via secure network connections, each retaining local control over EHR data while using a shared safety receipt service instance. Tenant-level isolation controls may be implemented to prevent cross-tenant data leakage while enabling anonymized benchmarking and aggregate analytics across tenants.

In some embodiments, safety receipt layer 130 and PoPC anchor client 140 are implemented as a set of stateless or minimally stateful microservices deployed in a containerized or virtualized environment, with per-tenant configuration state stored in isolated configuration stores. Such implementations can allow horizontal scaling of receipt generation and anchoring workloads across multiple processing nodes while preserving strict tenant-level isolation of patient identifiers and receipt data. For example, a load balancer may route DSI requests from different health systems 710A-710N to different instances of the safety receipt microservices, and tenant-specific encryption keys may be used to protect receipt payloads at rest and in transit. In some embodiments, anonymized benchmarking or aggregate analytics across tenants are computed from de-identified safety receipts or derived metrics, without exposing cross-tenant identifiers.

Figure 8:
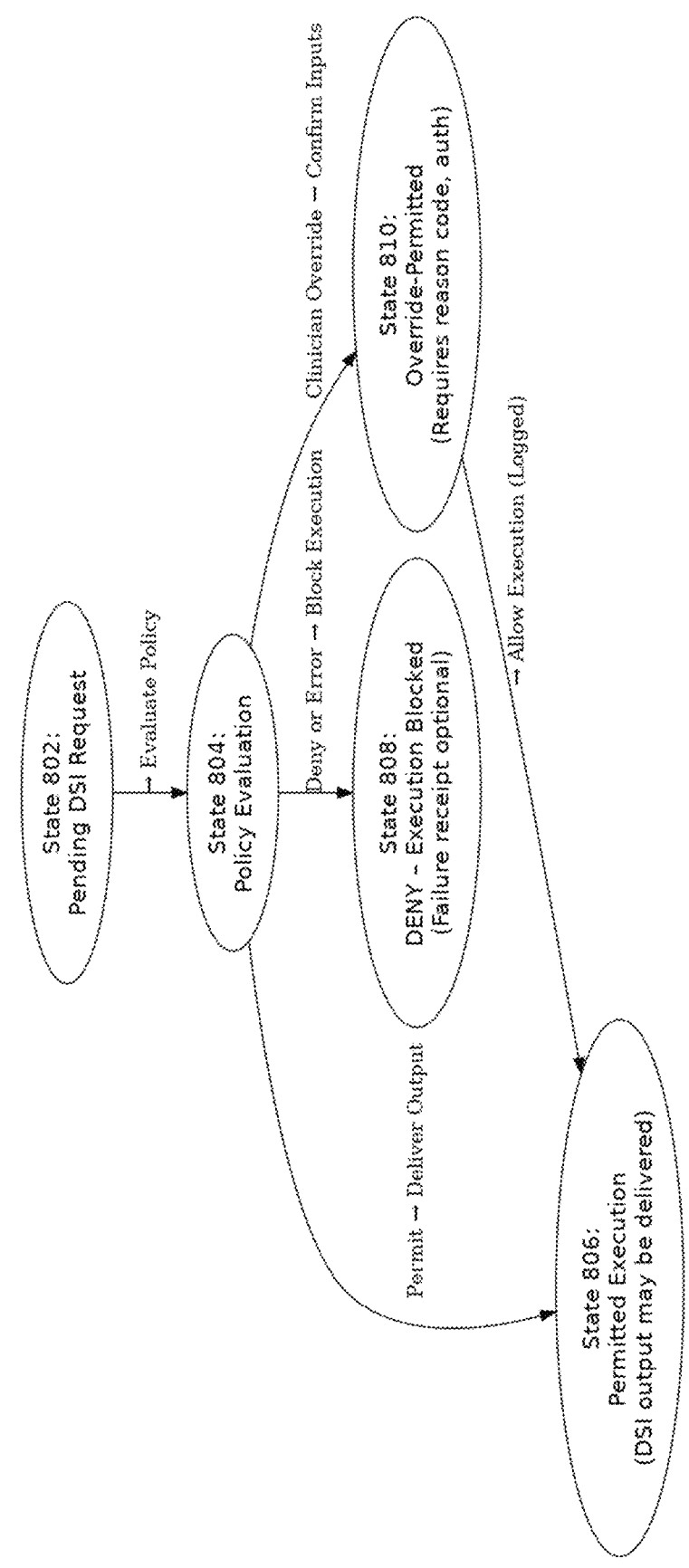
FIG. 8 is a state diagram illustrating fail-closed permit-before-action semantics enforced by the safety receipt layer, including example transitions among requested, permitted, guarded, overridden, denied, and failure-mode states for DSI episodes.

Fail-Closed Semantics (FIG. 8)

FIG. 8 illustrates an example state machine 800 for permit-before-action enforcement. Initial state 802 corresponds to a pending DSI request. From state 802, the system transitions to policy evaluation state 804. Upon successful evaluation and a permit outcome that satisfies a permit condition and, in some embodiments, an anchoring precondition, the system transitions to permitted execution state 806, from which a DSI output may be delivered or written back. If policy evaluation fails, a permit condition is not satisfied, or a required anchoring step cannot be completed, the system transitions to deny state 808, in which DSI execution is blocked. In some embodiments, the state machine 800 enforces a time-of-check-to-time-of-use latch that binds policy evaluation and anchoring to both clinician-facing render and EHR write-back paths, such that no DSI-initiated output or write-back is finalized until a permit or override satisfying the applicable predicates is recorded. In further embodiments, deny state 808 is associated with generation of a failure-mode safety receipt documenting that the DSI episode was blocked due to a failed permit condition or anchoring precondition.

In some embodiments, explicit clinician overrides are modeled as transitions requiring additional inputs (for example, override reason codes or secondary authentication) before allowing progression to an override-permitted state 810. Until the required override inputs are supplied and recorded, the state machine 800 remains in a pending or deny state and prevents delivery of the AI-assisted clinical recommendation or any associated DSI-initiated write-back, thereby maintaining fail-closed behavior for override paths. Each override transition may be captured and encoded in the safety receipt so that later reviewers can determine why an override was exercised, under which policy conditions it was exercised, and, in some embodiments, which clinician identifiers and timestamps were associated with the override.

Additional details of embodiments of the invention are described in the following sections and in the appended claims. The described components and operations are illustrative and non-limiting, and alternative implementations may reorder, merge, or subdivide components or steps while remaining within the scope of the claims.

In some embodiments, safety receipt layer 130 operates as one governance rail within a broader family of governance rails, including but not limited to trusted sensor ingress rails that emit Sensor Receipts (S2), trusted reality compositor rails that emit Reality Receipts (R2), and multi-harm safety risk budget engines that emit Safety Evidence Receipts. Optional cross-rail references recorded in a safety receipt 400 can provide an end-to-end chain of custody from upstream capture through AI-assisted decision support and downstream visualization or risk aggregation. Such cross-rail references are evidentiary only and, in at least some configurations, do not alter the internal permit-before-action semantics, permit outcomes, or fail-closed behavior enforced by safety receipt layer 130.

In some deployments, the HTI safety receipt layer operates as a decision-support or DSI-focused governance rail within a broader clinical AI safety governance stack that further includes trusted sensor ingress rails, trusted reality compositor rails, Safety Risk Budget Engines, revenue-cycle governance rails, and other specialized rails. In such configurations, each rail maintains its own internal gate predicates while exchanging evidentiary receipts, and the HTI safety receipt layer alone governs whether a DSI output may be produced or delivered for a given clinical episode. Upstream and downstream rails contribute sensor, visualization, or multi-harm risk evidence that may be referenced from safety receipts via cross-rail references without changing the HTI safety receipt layer's policy-graph evaluation, permit-before-action semantics, or fail-closed behavior.

As used herein, a "computer-readable medium" or "non-transitory computer-readable medium" refers to a physical storage medium configured to store instructions or data in a non-transitory manner, and excludes pure transitory propagating signals per se.

VIII. APPENDICES

Appendix A—Glossary of Terms

Agentic clinical workflow: A multi-step or agentic clinical decision support process in which one or more autonomous or semi-autonomous agents orchestrate a sequence of DSIs, retrieval operations, or documentation steps, each step treated as a bounded DSI episode or sub-episode subject to the same permit-before-action and fail-closed semantics enforced by the safety receipt layer.

AI-assisted clinical recommendation: A recommendation, score, alert, summary, or other output generated by a machine learning model, rules engine, or other artificial intelligence component to support clinical decision making.

AI-governed billing gate: A gate or middleware component configured to detect AI-influenced billing events, evaluate safety receipt preconditions for such events, and enforce permit-before-bill, fail-closed semantics by blocking or routing non-compliant AI-influenced billing events to manual review, without altering the safety receipt layer's core gate predicates.

AI-influenced billing event: A billing record, claim line, or related revenue-cycle artifact in which a code, modifier, or billing attribute was inserted, adjusted, or recommended by a clinical decision support intervention, coding engine, or summarization engine. AI-influenced billing events can be used by a revenue-cycle governance rail to decide whether safety-receipt based preconditions must be evaluated. References to AI-influenced billing events in the present application are evidentiary only and do not alter clinical gate predicates enforced by the safety receipt layer.

Anchoring precondition: A precondition that requires successful anchoring of a safety receipt or a digest thereof to a tamper-evident audit store before finalizing or delivering an AI-assisted clinical recommendation or any associated DSI-initiated write-back for a DSI episode.

Append-only verifiable log: A logging or audit structure that accepts only append operations and publishes signed heads together with inclusion and consistency proofs, allowing external verifiers to detect omission or reordering of entries.

Benchmark rating indicator: As used herein, "benchmark rating indicator" means a derived metric or composite score computed from cross-tenant aggregate metrics over safety receipts for a DSI family or DSI type, used to characterize relative safety, burden, or fairness performance of a tenant, deployment, or program. Benchmark rating indicators are evidentiary overlays only and do not alter the policy-graph evaluation, permit-before-action semantics, or fail-closed behavior enforced by the safety receipt layer; the claims control.

Billing-governance receipt (AI-governed revenue-cycle truth receipt): A structured, machine-verifiable revenue-cycle governance receipt that binds an AI-influenced billing event to one or more safety receipt identifiers, an evaluated permit outcome, and a billing disposition (for example, submitted, auto-adjudicated, routed to manual review, or blocked). Billing-governance receipts are stored in a revenue-cycle governance store and are evidentiary only; they do not alter permit-before-action or fail-closed predicates enforced by the safety receipt layer.

Clinical AI Risk & Change-Control Rail: A separate governance rail configured to emit risk- and change-control receipts summarizing risk tier, hazard classifications, change-control or PCCP event identifiers, responsible owner identifiers, and mitigation status for a DSI type or model configuration. The Clinical AI Risk & Change-Control Rail operates outside the EHR-DSI invocation path and may be referenced by safety receipts for evidentiary purposes only.

Clinical context envelope: A structured bundle of data representing the salient context of a DSI episode, which may include patient state, encounter metadata, user metadata, and DSI-type metadata.

Clinical decision support intervention (DSI): Any automated or semi-automated function that evaluates patient data and produces a recommendation, alert, or guidance intended to inform clinical decisions. Examples include, without limitation: sepsis risk scoring DSIs, imaging triage and reporting DSIs, digital pathology DSIs, technology-enabled chronic care DSIs, AI-assisted intra-body robotic navigation and intervention DSIs, and therapy-planning DSIs for high-risk biologic and interventional therapies such as gene therapies, cell therapies, programmable RNA-based therapeutics, and neuromodulation or implant programming procedures.

Consistency proof: A cryptographic proof that a newer signed head of an append-only verifiable log extends a prior signed head without modification of previously committed entries.

Cross-rail reference: An optional pointer in a safety receipt to one or more external governance receipts (for example, Sensor Receipts (S2) from a trusted sensor ingress rail, Reality Receipts (R2) from a trusted reality compositor, Safety Evidence Receipts from a Safety Risk Budget Engine, risk- and change-control receipts from a Clinical AI Risk & Change-Control Rail, or revenue-cycle governance receipts from a revenue-cycle governance rail). Cross-rail references are evidentiary only and do not alter the safety receipt layer's gate conditions, permit outcomes, permit-before-action semantics, or fail-closed behavior.

DSI episode: A bounded invocation of a clinical decision support intervention (DSI) for a particular patient or encounter, treated as the unit of record for the safety receipt layer and describing, in structured form, at least the contextual inputs, applicable policies or identifiers thereof, the resulting permit outcome, and, in some embodiments, associated DSI outputs and clinician responses.

DSI transparency profile: A machine-readable profile or template that captures transparency attributes and documentation hooks for a particular clinical decision support intervention (DSI) family, version, or deployment, including one or more framework or profile identifiers, references to model cards or risk-management plans, and other governance metadata that may be referenced from safety receipts (for example, via regulatory or transparency_mapping fields) without altering permit-before-action or fail-closed semantics enforced by the safety receipt layer.

Evidence bundle: A machine-readable summary keyed by one or more monitoring-profile identifiers and aggregation windows that aggregates metrics, counts, and references to underlying safety receipts for transparency, oversight, or payer programs. Evidence bundles are evidentiary only and do not alter permit-before-action or fail-closed predicates enforced by the safety receipt layer.

Fail-closed: A property of a system whereby, upon occurrence of a failure condition, the system transitions to a safe state that blocks or limits potentially unsafe actions.

Failure-mode safety receipt: A safety receipt generated for a DSI episode that did not proceed normally, for example because a permit condition or anchoring precondition was not satisfied, the safety receipt documenting that the episode was denied or blocked under permit-before-action and fail-closed semantics.

Governance outcome: A policy or operational action triggered by monitoring thresholds or governance review, such as tightening one or more permit predicates, pausing a DSI variant, downgrading an autonomous mode to decision-support, or opening a safety review. Governance outcomes are evidentiary only and are applied outside the real-time gate; they do not alter the safety receipt layer's core gate semantics as claimed.

Governance receipt: A structured, machine-verifiable evidence object emitted by an external governance rail, such as a trusted sensor ingress rail, a trusted reality compositor, a Safety Risk Budget Engine, a Clinical AI Risk & Change-Control Rail, or a revenue-cycle governance rail, describing governance- or safety-related information for one or more clinical or AI-assisted episodes. Governance receipts may be referenced by safety receipts via cross-rail references for evidentiary purposes only and do not alter the safety receipt layer's gate conditions or permit outcomes.

Hash-based message authentication code (HMAC): As used herein, "hash-based message authentication code (HMAC)" refers to a keyed construction of a cryptographic hash function with a symmetric key, used to derive pseudonymous identifiers or authentication tags without exposing underlying direct identifiers.

Health IT transparency requirement: A documentation or disclosure requirement imposed by a regulator, certification program, or accrediting body, typically requiring description of data inputs, logic, risks, and mitigations associated with a DSI.

HTI profile: A profile or template identifying a subset of safety receipt fields, policy graph nodes, monitoring indicators, and cross-rail references that are required or recommended for a given DSI family (for example, sepsis risk scoring, imaging triage, or LLM-based discharge planning assistants) in order to satisfy a corresponding health IT transparency, certification, or oversight framework.

HTI-ready: In some embodiments, a configuration of a safety receipt layer in which one or more safety receipt fields are mapped, via one or more transparency profiles or mapping profiles, to documentation, disclosure, or reporting elements required by a health IT transparency, certification, or oversight framework. HTI-ready configurations can enable the same structured safety receipts to serve both as episode-level execution records and as machine-readable evidence for such frameworks.

Idempotency token: A unique token binding a permit and its associated finalization attempt so that retries cannot produce duplicate or split-brain render/write-back finalizations across distributed systems.

Imaging triage DSI: A clinical decision support intervention configured to process medical images, such as radiology or pathology images, and to output triage, prioritization, or detection flags, potentially for multiple target finding types within a single study or image series.

Inclusion proof: A cryptographic proof that a given entry, digest, or safety receipt is included in a particular signed head of an append-only verifiable log.

Insights and monitoring module: A component configured to ingest safety receipts and compute aggregate metrics, dashboards, or reports describing DSI usage, permit outcomes, overrides, alert burden, performance, fairness, or safety incidents across a population of DSI episodes.

Maximum-merge-delay (MMD): A freshness policy for an append-only verifiable log that bounds the maximum time or number of operations between acceptance of an entry and publication of a signed head under which that entry is provably included.

Monitoring (post-market) profile: A machine-readable configuration that defines monitored fields, aggregation windows, population-segment filters, thresholds, and report formats for post-market monitoring of DSI usage, performance, safety, fairness, or burden. Monitoring profiles are consumed by an insights and monitoring module and are evidentiary only; they do not relax or modify permit-before-action or fail-closed predicates enforced by the safety receipt layer.

Patient truth and rights rail: A governance rail or interface layer that consumes safety receipts and generates patient- or proxy-facing explanation records, rights records, and case bundles for AI-assisted DSI episodes, including support for re-evaluation requests, appeals, and patient preference entries, without altering permit-before-action or fail-closed predicates enforced by the safety receipt layer.

Permit condition: A predicate or set of predicates that must be satisfied for a permit outcome to authorize execution of a DSI episode, for example requiring that the permit outcome corresponds to a permitted state (such as permit or permit with guardrails) and that any applicable anchoring precondition is satisfied.

Permit outcome: A decision computed by a policy graph evaluation engine indicating whether a requested DSI episode is permitted, permitted with guardrails, requires explicit override, or denied.

Permit validity (TTL): A validity interval associated with a permit outcome, during which render and write-back finalization are allowed. When the interval elapses without finalization, the permit condition is treated as unsatisfied and the episode transitions to a deny or failure path.

Permit-before-action: A semantic pattern in which an action may only be executed upon issuance of an affirmative permit outcome satisfying a permit condition.

Policy digest/Policy signature: A cryptographic digest and, when available, a digital signature over a policy graph or policy profile used to bind a safety receipt to a specific, attested policy version.

Policy graph: A representation, such as a directed graph or rule set, encoding policy conditions, thresholds, and routing logic used to determine a permit outcome for a DSI episode.

Policy-evaluation proof reference: A field, such as policy_evaluation_proof_ref, that carries a pointer to verifiable artifacts or logs associated with a policy-evaluation step for a DSI episode. Policy-evaluation proof references are evidentiary only and do not alter the underlying policy-graph evaluation or gate predicates; the claims control.

PoPC anchor client: A component of the safety receipt layer configured to transmit safety receipts or derived cryptographic digests to one or more tamper-evident audit stores, such as append-only verifiable logs or external compliance registries, thereby anchoring proof-of-policy-compliance artifacts under a freshness or integrity policy.

Population segment: A subset of DSI episodes or patients defined by shared attributes, such as age range, diagnosis category, comorbidity profile, socioeconomic indicator, or other clinically or ethically relevant characteristic, used for stratified analyses of DSI usage, performance, or fairness.

Proof-of-policy-compliance (PoPC): Evidence demonstrating that a DSI episode was executed in conformance with one or more applicable policies, as encoded in a safety receipt.

Reality Receipt (R2): An optional evidence object emitted by a trusted reality compositor that canonically identifies an overlay, binds it to a scene or image context, and carries policy predicates and associated proofs. A safety receipt may reference one or more reality receipts corresponding to visualization of a DSI episode, for audit purposes only.

Receipt signature/Key ID: A digital signature computed over a safety-receipt payload and an identifier of the signing key used for rotation, enabling tamper detection and key-rotation management for receipts.

Revenue-cycle governance rail/Revenue Cycle Truth Receipt: A governance rail or subsystem configured to generate structured, machine-verifiable revenue-cycle governance receipts (sometimes referred to as Revenue Cycle Truth Receipts) that bind billed clinical events, procedure codes, payer or coverage identifiers, and, optionally, reimbursement modifiers to underlying clinical episodes and associated safety receipts. Safety receipts may carry cross-rail references to such revenue-cycle governance receipts for evidentiary purposes only; revenue-cycle governance rails do not alter the safety receipt layer's gate conditions, permit outcomes, permit-before-action semantics, or fail-closed behavior.

Revocation ID: An identifier recorded when a previously issued permit is revoked under a governance or anchoring process; verifiers treat any permit associated with an active revocation id as invalid.

Rights receipt: A structured, machine-verifiable record that references a safety receipt identifier and encodes at least a rights-type identifier, a request timestamp, an actor role identifier, and a disposition, suitable for anchoring in a tamper-evident audit store for patient- or proxy-exercised rights.

Risk- and change-control receipt: An optional evidence object emitted by a Clinical AI Risk & Change-Control Rail that records risk- and change-control metadata for a DSI type or model configuration (for example, a risk tier, hazard classification, change-control or PCCP event identifiers, responsible owner identifiers, and mitigation status). References to such receipts do not alter permit-before-action semantics or fail-closed behavior enforced by the safety receipt layer.

Role-based receipt view: A policy-governed representation of a safety receipt or an aggregate derived therefrom that is tailored to a particular role or actor, such as a treating clinician, quality analyst, payer, or oversight body, and that may include redaction, pseudonymization, or aggregation of certain fields.

Safety Evidence Receipt: A structured, machine-verifiable evidence object emitted by a Safety Risk Budget Engine that summarizes multi-harm safety, risk, and incident information for one or more AI-assisted clinical episodes. A safety receipt may include one or more cross-rail references to associated Safety Evidence Receipts for oversight or audit purposes; such references are evidentiary only and do not alter the safety receipt layer's gate conditions or permit outcomes.

Safety receipt: A structured, machine-readable record for a DSI episode that captures at least a clinical context envelope, one or more identifiers of applicable policies or policy graph nodes, a permit outcome and any associated guardrails or override codes, and, in some embodiments, anchoring or cross-rail reference fields. Safety receipts are emitted by the safety receipt layer and may serve both as episode-level execution records and as proof-of-policy-compliance artifacts.

Safety receipt layer: A logical or physical component interposed between an EHR system and one or more DSI engines, configured to capture context, evaluate policy graphs, enforce permit-before-action and fail-closed semantics for DSI episodes, generate safety receipts, and, in some embodiments, anchor proofs-of-policy-compliance to one or more tamper-evident audit stores.

Safety Risk Budget Engine: A governance rail or module configured to aggregate safety signals across multiple DSI episodes into a multi-harm risk vector, enforce risk budgets or thresholds, and emit Safety Evidence Receipts suitable for oversight, post-market monitoring, or tribunal-grade review. Safety Risk Budget Engines may consume safety receipts as evidence inputs and are logically distinct from, but interoperable with, the safety receipt layer.

Sensor Receipt (S2): An optional evidence object emitted by a trusted sensor ingress rail (for example, a Trusted Sensor Ingress Layer (TSIL) or TSIL-Scan medical-imaging ingress gateway) that describes a sensor or imaging event and its anchoring under a freshness policy. A safety receipt may include one or more evidentiary references to such sensor receipts for end-to-end chain-of-custody, without changing permit-before-action semantics enforced by the safety receipt layer.

Signed head: A cryptographic summary of the current state of an append-only verifiable log, signed by or on behalf of a log operator and used as a reference for inclusion and consistency proofs.

Status stapling: A freshness mechanism in which a safety receipt carries, in addition to its own payload, a status tuple derived from an anchoring event in an append-only verifiable log, including at least a signed_head_id, a head_timestamp, and a staleness_interval. Status stapling enables downstream verifiers to validate maximum-merge-delay (MMD) freshness and log consistency at review time without re-running the anchoring protocol and is evidentiary only, without altering permit-before-action semantics or fail-closed behavior enforced by the safety receipt layer.

Tamper-evident audit store: A storage system configured such that alteration or deletion of stored entries is detectable, for example via append-only semantics, cryptographic hashes, chained integrity mechanisms, or implementation as an append-only verifiable log that publishes signed heads and supports inclusion and consistency proofs under a maximum-merge-delay (MMD) freshness policy.

Time-of-check-to-time-of-use (TOCTOU) latch: A control mechanism that binds policy evaluation and, in some embodiments, anchoring to render and write-back finalization, such that neither clinician-facing render nor DSI-initiated write-back can be finalized until a corresponding permit or override satisfying applicable predicates has been recorded.

Transparency and certification rail: As used herein, "transparency and certification rail" means a service or subsystem configured to consume safety receipts generated under permit-before-action, fail-closed semantics; resolve safety receipt fields and associated documentation references against DSI transparency profiles, framework profiles, and, in some embodiments, monitoring profiles; and generate machine-readable and/or human-readable evidence exports for health IT transparency, certification, or AI-governance frameworks. Transparency and certification rails operate as evidentiary overlays only and do not alter the policy-graph evaluation, permit-before-action semantics, or fail-closed behavior enforced by the safety receipt layer; the claims control.

Trusted reality compositor: A separate compositor rail or OS module configured to gate rendering of synthetic overlays on clinical or imaging views based on per-overlay reality receipts, to inject machine-readable labels on the render surface, and to emit receipts describing what was rendered under which policy predicates. The reality compositor is logically distinct from, but may interoperate with, the safety receipt layer.

Trusted sensor ingress rail: A separate system or layer configured to admit sensor or imaging events under a freshness policy and to emit per-event or per-study sensor receipts attesting to properties of the underlying acquisition (for example, acquisition time, calibration posture, or anchoring to an append-only log). Such rails may operate at the sensor bus, modality console, or a medical-imaging gateway and are logically distinct from the safety receipt layer.

Appendix B—Example Safety Receipt Schema

The following illustrates an example JSON-like schema for a safety receipt. The schema is illustrative and non-limiting. Field names, nesting, and value types are provided as examples; implementations may add, omit, or rename fields while remaining within the scope of the claims, provided that a safety receipt encodes, in structured form, at least: (i) a clinical context envelope, (ii) applicable policies or identifiers thereof, and (iii) a permit outcome for a DSI episode. Example JSON-like schema (illustrative, non-limiting):

Notes (illustrative, non-limiting): for readability, the JSON-like example below omits inline comments.

encounter_type: inpatient, outpatient, emergency care_setting: ED, ICU, ward, ambulatory dsi_family: risk_score, imaging_triage, llm_assistant clinician_decision: accepted, accepted_with_modifications, deferred, rejected, ignored severity: low, medium, high; example event_tags: near_miss, adverse_event signature_value is a signature over the receipt payload; context_field_list_digest is a hash over a canonicalized representation of the listed fields.

Program metadata, if present, is evidentiary-only and does not alter gate predicates.

```
{
  "schema version": "HTI-Receipt-1.0",
  "receipt_id": "sr-2025-11-001234",
  "creation_timestamp": "2025-11-27T14:32:05Z",
  "subject": {
    "patient_hash": "H_3af9c1...",
    "encounter_id_hash": "E_d1f92a...",
    "encounter_type": "inpatient",
    "care_setting": "ED",
    "organization_id_hash": "ORG_0291..."
  },
  "dsi": {
    "dsi_type": "sepsis_risk_score_v3",
    "dsi_family": "risk_score",
    "dsi version": "3.1.0",
    "dsi_vendor_id": "VENDOR_ACME_MED",
    "dsi_instance_id": "INST-HTI-SEPSIS-001"
  },
  "context": {
    "triggering_event": "open_order_entry",
    "trigger_timestamp": "2025-11-27T14:31:59Z",
    "anonymized_patient_id": "P_81ff9d...",
    "encounter_type": "inpatient",
    "vitals": {
      "hr": 120,
      "bp_systolic": 88,
      "bp_diastolic": 52,
      "temp_c": 39.2,
      "resp_rate": 24,
      "spo2": 92
    },
    "labs": {
      "wbc": 18.5,
      "lactate": 3.2
    },
    "active_diagnoses": ["pneumonia"],
```

```
          "active_medications": ["ceftriaxone"],
          "recent_procedures": [ ],
          "user": {
             "clinician_role": "attending_physician",
             "clinician_id_hash": "U_4c19e7...",
             "department": "Emergency Medicine",
             "location": "ED-01"
          },
          "dsi_metadata": {
             "dsi_type": "sepsis_risk_score_v3",
             "trigger_channel": "EHR-embedded",
             "session_id_hash": "S_11b3cf..."
          }
       }
       "policy": {
       "policy_graph_id": "PG-HTI-SEPSIS-1.2",
       "policy_version": "1.2.0",
       "policy_profile_id": "HTI-Core-Sepsis-Adult/1.2",
       "policy_digest": "PDIG_9aa0...",
    "policy_signature": "PSIG_b21e...",
    "policy_evaluation_proof_ref": "PEVAL 4c9d...",
       "evaluation_outcome": "permit_with_guardrails",
       "constraints_applied": [
          "require_confirmatory_order_review",
          "label_high_risk_output"
       ],
       "excluded_population_rules_triggered": [ ],
       "evidence_refs": [
          "log://hti/policy_eval/2025/11/27/evt-983141"
       ]
    },
       "permit": {
       "permit_outcome": "permit_with_guardrails",
       "permit_reason_code": "PERMIT_HIGH_RISK_WITH_GUARDRAILS",
       "override_required": false,
       "override_type": null,
       "override_reason_code": null,
       "requested_behavior_mode": "decision_support",
       "effective_behavior_mode": "decision_support",
       "permit_validity_ms": 30000,
       "revocation_id": null
    },
       "agentic": {
          "workflow_id": "wf-2025-11-ABCD",
          "step_id": "step-003",
          "parent_episode_id": "sr-2025-11-000123",
          "dependencies": ["sr-2025-11-000120", "sr-2025-11-000121"],
          "agent_role": "review_summarizer"
       "dsi_output_summary": {
          "output_type": "risk_score",
          "risk_score": 0.92,
          "risk_category": "high_risk",
          "recommended_actions": [
             "sepsis_bundle_order_set",
             "lactate_repeat_in_4h"
          ],
          "free text_summary_hash": "TXT_91ad3c..."
       },
    "clinician_response": {
       "response_type": "accepted_with_modifications",
       "response_timestamp": "2025-11-27T14:35:10Z",
       "actions_taken": [
          "ordered_sepsis_bundle",
          "added_additional_antibiotic"
       ],
       "override_applied": false,
       "override_reason_code": null,
       "secondary_auth_id": "U2F_0x9c...",
       "notes_hash": "N_91fe2b..."
    },
       "monitoring": {
          "alert_burden_bucket": "high",
          "episode_risk_bucket": "high_risk",
          "incident_flags": [ ],
          "safety_review_queue": false,
          "population_segments": [
             "age_65_74",
             "respiratory_infection"
          ],
```

```
        "evidence_bundle": null
    },
"anchor": {
    "local_log_id": "LL-2025-11-000987",
    "ehr_audit_row_id": "EHR_AUD_55421",
    "signed_head_id": "HEAD_7f3c...",
    "head_signature": "SIG_ab12...",
"status_tuple": {
    "signed_head_id": "HEAD_7f3c...",
        "head_timestamp": "2025-11-27T14:32:06Z",
        "staleness_interval_ms": 4800
    },
    "external_digest": "D_418e79...",
    "receipt_signature": "RSIG_e1f3...",
    "key_id": "K_2025Q4_rot01",
    "proof_bundle": {
        "inclusion_proof": "INC_...",
        "consistency_proof": "CONS_...",
        "log_chain_position": "block_height_182734",
        "integrity_proof_type": "hash_chain",
        "integrity_proof_payload_hash": "H_9a21ff...",
        "mmd_ms": 5000
    }
},
"program": {
        "chronic_care_program_id": "ACCESS-CRM-HTN-2026",
        "outcome_window_days": 180,
        "outcome_measure_refs": [
            "bp_control_rate",
            "a1c_improvement",
            "exacerbation_free_days"
        ],
        "tempo_device_study_id": "TEMPO-HTN-001"
    },
    "cross_rail": {
        "sensor_receipt_refs": ["s2:2025-11-CT-000123"],
        "reality_receipt_refs": ["r2:2025-11-OVL-000987"],
        "safety_evidence_receipt_refs": ["sev:2025-11-SRBE-000045"],
        "revenue_cycle_truth_receipt_refs": ["rcm:2025-11-HTI-RCM-000123"],
        "ingress_profile": "med_imaging_gateway/1.0",
        "compositor_profile": "clinical_viewer_overlay/1.0"
    },
    "provenance": {
        "context_field_list": [
            "context.vitals.hr",
            "context.vitals.bp_systolic",
            "context.labs.wbc",
            "context.labs.lactate",
            "context.active_diagnoses",
            "context.active_medications",
            "context.user.clinician_role",
            "context.dsi_metadata.dsi_type"
        ],
        "context_field_list_digest": "CFD_9b21ff..."
    },
    "transparency_mapping": {
        "data_inputs_ref": [
            "context.vitals",
            "context.labs",
            "context.active_diagnoses",
            "context.active_medications"
        ],
        "algorithm_id_ref": [
            "dsi.dsi_type",
            "dsi.dsi_version",
            "policy.policy_graph_id",
            "policy.policy_version"
        ],
        "guardrails_ref": [
            "policy.constraints_applied",
            "permit.permit_outcome",
            "permit.effective_behavior_mode"
        ],
        "monitoring_indicators_ref": [
            "monitoring.alert_burden_bucket",
            "monitoring.incident_flags",
            "monitoring.population_segments"
        ]
    }
```

-continued

```
"regulatory": {
    "framework_profile_ids": [
        "HTI-DSI-Transparency/Core-Sepsis-Adult/1.0",
        "AI-HighRisk-Imaging/Local-Policy-Profile/1.0"
    ],
    "dsi_transparency_profile_id": "HTI-DSI-Sepsis-Profile-1.0",
    "plain_language_intent_ref": "doc://hti/sepsis/plain_language_summary",
    "training_data_summary_ref": "doc://developer/model_card/sepsis_v3/training_summary",
    "validation_dataset_ref": "doc://developer/model_card/sepsis_v3/validation_summary",
    "known_limitations_ref": "doc://developer/model_card/sepsis_v3/limitations",
    "risk_management_plan_id": "RMP-Sepsis-Adult-1.0",
    "post_market_monitoring_plan_id": "PMM-Sepsis-Adult-1.0",
    "quality_management_system_ref": "QMS-Cert-ISO13485-ACME-MED-2025-01",
    "pccp_version_id": "PCCP-Sepsis-Adult-1.0",
    "learning_event_id": "LE-2025-11-001",
    "pre_change_performance_snapshot_ref": "metrics://sepsis_v3/perf/pre_LE-2025-11-001",
    "post_change_delta_summary_ref": "metrics://sepsis_v3/perf_delta/post_LE-2025-11-001"
}
"extensions": {
    "vendor_private": { },
    "site_specific": { }
}
}
```

In some embodiments, a safety receipt further includes an optional program object carrying evidentiary metadata for outcomes-based chronic-care payment models or digital health real-world evidence pilots, such as chronic_care_program_id, outcome_window_days, outcome_measure_refs, and, in some deployments, a tempo_device_study_id linking episodes to device-level studies. These fields are evidentiary-only overlays and do not alter the permit-before-action semantics, fail-closed behavior, or core gate predicates enforced by the safety receipt layer; the claims control.

In some embodiments, a safety receipt may additionally include a "cross_rail" object carrying optional references to external governance receipts, such as Sensor Receipts (S2) emitted by a trusted sensor ingress rail, Reality Receipts (R2) emitted by a trusted reality compositor, Safety Evidence Receipts emitted by a Safety Risk Budget Engine, or risk- and change-control receipts emitted by a separate Clinical AI Risk & Change-Control Rail. Such cross-rail references are evidentiary only and do not alter the policy-graph evaluation, the permit-before-action semantics, or the fail-closed behavior enforced by the safety receipt layer.

In some embodiments, the "permit" object further encodes the behavior mode requested by a DSI (for example, "requested_behavior_mode": "autonomous_imaging") and the mode actually permitted for that episode (for example, "effective_behavior_mode": "decision_support"). This allows autonomous imaging behaviors (such as auto-normal chest radiograph triage or auto-finalizing draft reports) to be governed under a tethered model in which the requested behavior and the permitted behavior remain observable at the episode level.

In another example, a safety receipt for an imaging triage DSI may include additional context fields such as an imaging modality (for example, CT, MRI, ultrasound), a body region (for example, abdomen-pelvis, chest), and a list of triage target classes and corresponding triage flags (for example, small_bowel_obstruction, free_air, aortic_aneurysm) within the "context" and "dsi_output_summary" objects, while still conforming to the same overall structure shown above. For instance, a multi-condition radiology triage model for abdomen-pelvis CT studies may populate fields describing which urgent findings were evaluated and which, if any, were flagged for expedited review, together with the permit outcome and any guardrails applied by the policy graph.

In various embodiments:

Fields in the "subject", "dsi", "context", "policy", "permit", "dsi_output_summary", "clinician_response", and "anchor" objects may constitute a core profile for a safety receipt layer, whereas "monitoring", "agentic", "cross_rail", "transparency_mapping", "regulatory", and "extensions" objects may be optional or profile-dependent.

The "cross_rail" object may include optional references to records emitted by external governance rails, such as Sensor Receipts (S2) emitted by a trusted sensor ingress rail, Reality Receipts (R2) emitted by a trusted reality compositor, Safety Evidence Receipts emitted by a Safety Risk Budget Engine, risk- and change-control receipts emitted by a Clinical AI Risk & Change-Control Rail, or Revenue Cycle Truth Receipts emitted by a revenue-cycle governance rail. Such cross-rail references are evidentiary only and do not alter the safety receipt layer's policy-graph evaluation, permit-before-action semantics, or fail-closed behavior.

The "transparency_mapping" object may be used to map safety receipt fields to documentation elements required by one or more health IT transparency or certification frameworks, thereby allowing the same underlying safety receipts to support both episode-level reconstruction of a DSI episode and aggregate monitoring or reporting of DSI usage, safety, and fairness.

The "regulatory" object may be used to carry profile identifiers and references to documentation, risk-management plans, or post-market monitoring plans associated with one or more health IT transparency, certification, or AI-governance frameworks, including, by way of example and not limitation, criteria issued by national health IT coordinators, obligations for high-risk AI systems under applicable AI legislation, or adaptive machine-learning change-control plans. Such "regulatory" fields are evidentiary-only overlays and do not alter the permit-before-action semantics or fail-closed behavior enforced by the safety receipt layer; the claims control, and gate predicates remain defined in the core Specification.

Implementations may define one or more conformance profiles identified, for example, by "policy_profile_id"

or an external profile identifier, each specifying which subsets of fields are required, recommended, or optional for a given DSI family (for example, sepsis risk scoring, imaging triage, LLM-based discharge planning assistants, or chronic disease management DSIs).

Context provenance and verification

Example transparency elements:

Ability to demonstrate which EHR and DSI metadata fields were included in the clinical context envelope at the time of policy evaluation.

Ability to cryptographically verify that the permit outcome recorded in a safety receipt was generated from that clinical context envelope.

Mapped to (illustrative):

provenance.context_field_list provenance.context_field_list_digest

In some profiles, a provenance object is recommended or required for high-assurance auditing, while remaining an optional overlay on top of the core safety receipt structure.

Appendix C—Example Field Mapping to Transparency Elements

This Appendix illustrates, in an illustrative and non-limiting manner, how fields in a safety receipt may be mapped to documentation or disclosure elements required by one or more health IT transparency, certification, or oversight frameworks. Actual mappings may vary by framework, jurisdiction, or institutional policy. Field paths are expressed using a dotted notation consistent with the example schema of Appendix B.

Data inputs and patient context

Example transparency elements:

Description of data inputs used by the DSI.

Clinical context and limitations of input data.

Mapped to (illustrative):

subject.care_setting context. vitals context.labs context.active_diagnoses context.active_medications context.recent_procedures context.encounter_type context.user.clinician_role context.dsi_metadata.modality context.dsi_metadata.body_region monitoring.population_segments Algorithm identity, version, and configuration Example transparency elements:

Algorithm name and version.

Vendor or developer identity.

Configuration or deployment profile.

Mapped to (illustrative):

dsi.dsi_type dsi.dsi_family dsi.dsi_version dsi.dsi vendor_id dsi.dsi_instance_id policy.policy_graph_id policy.policy_version policy.policy_profile_id Intended use, indications, and safeguards Example transparency elements:

Intended use population and indications.

Contraindications or excluded populations.

Safeguards, guardrails, and required labeling.

Whether the DSI is used in decision-support vs. autonomous modes.

Mapped to (illustrative):

policy.policy_profile_id policy.constraints_applied policy.excluded_population_rules_triggered permit.permit_outcome permit.permit_reason_code permit.requested_behavior_mode permit.effective_behavior mode monitoring.episode_risk_bucket monitoring.alert_burden bucket Monitoring, performance, and incident logging Example transparency elements:

Monitoring plan and performance indicators.

Incident, near-miss, or adverse-event logging.

Burden and utilization metrics (for example, alert burden).

Fairness and disparity monitoring across population segments.

Mapped to (illustrative):

monitoring.incident_flags monitoring.safety_review_queue monitoring.alert_burden_bucket monitoring.population_segments monitoring.evidence_bundle clinician_response.response_type clinician_response.actions_taken aggregated statistics derived from permit.permit_outcome aggregated statistics derived from clinician_response.response_type aggregated statistics derived from Safety Evidence Receipts referenced via cross_rail.safety_evidence_receipt_refs Human oversight, overrides, and human-in-the-loop behavior Example transparency elements:

Description of how clinicians interact with the DSI.

Frequency and reasons for overrides.

Human-in-the-loop safety mechanisms.

Mapped to (illustrative):

permit.override_required permit.override_type permit.override_reason_code clinician_response.response_type clinician_response.override_applied clinician_response.override_reason_code clinician_response.notes_hash Provenance, anchoring, and auditability Example transparency elements:

Audit trail and provenance of DSI recommendations.

Mechanisms for tamper-evident logging.

Ability to reconstruct episodes for investigation.

Mapped to (illustrative):

subject.patient_hash subject.encounter_id_hash subject.organization_id_hash anchor.local_log_id anchor.ehr_audit_row_id anchor.external_digest anchor.signed_head_id anchor.status_tuple.head_timestamp
anchor.status_tuple.staleness_interval_ms
anchor.proof_bundle.inclusion proof
anchor.proof_bundle.consistency_proof
anchor.proof_bundle.log_chain_position
anchor.proof_bundle.integrity_proof_type
anchor.proof_bundle.integrity_proof_payload_hash
anchor.proof_bundle.mmd_ms
anchor.receipt_signature
anchor.key_id
policy.evidence_refs End-to-end governance rails and chain-of-custody
Example transparency elements:
Description of how upstream data capture and down-stream visualization are governed.
Evidence of end-to-end chain-of-custody from capture through DSI and visualization, and onward to risk aggregation.
Mapped to (illustrative):
cross_rail.sensor_receipt_refs
cross_rail.reality_receipt_refs
cross_rail.safety_evidence_receipt_refs
cross_rail.revenue_cycle_truth_receipt_refs
cross_rail.ingress_profile
cross_rail.compositor_profile Transparency mapping object
Example transparency elements:
Explicit mapping from receipt fields to regulatory or certification documentation elements.
Machine-readable representation of how receipts satisfy framework requirements.
Mapped to (illustrative):
transparency_mapping.data_inputs_ref
transparency_mapping.algorithm_id_ref
transparency_mapping.guardrails_ref
transparency_mapping.monitoring_indicators_ref In various embodiments, implementers may define one or more transparency profiles or templates, each specifying how a given set of transparency or certification elements is mapped to a subset of the safety receipt fields for a particular DSI family (for example, sepsis risk scoring, imaging triage, or LLM-based discharge planning assistants). These mappings are illustrative and evidence-only; they do not alter the permit-before-action semantics or fail-closed behavior enforced by the safety receipt layer, and the scope of the invention remains defined by the claims and the core Specification.

Appendix D—Example Policy Graph Snippet

This Appendix provides an illustrative and non-limiting example of a policy graph for a sepsis risk DSI and, by extension, illustrates how similar policy graphs may be defined for other DSI families such as imaging triage DSIs. The example is expressed as a set of nodes with conditions and actions; in practice, policy graphs may be encoded using rules engines, decision tables, graph structures, or other representations.

Example: Sepsis Risk DSI Policy Graph Nodes

Node: requires_minimum data
Purpose:
Ensure that a minimum set of required clinical inputs is present before allowing DSI execution.

Example condition:
lactate and white blood cell count (WBC) present within last 24 hours.
Example evaluation:
If condition is false:
Set policy.evaluation_outcome="deny".
Set permit.permit_outcome="deny".
Optionally set monitoring.incident_flags to include "data_insufficient".
If condition is true:
Proceed to next node (excluded_population).

Node: excluded_population
Purpose:
Prevent use of an adult sepsis model in excluded populations or indications.
Example condition:
patient age <18 OR pregnancy flag=true.
Example evaluation:
If condition is true:
Either route to a pediatric/obstetric DSI variant or set:
policy.evaluation_outcome="deny".
permit.permit_outcome="deny".
Optionally set policy.excluded_population_rules_triggered to include "pediatric_or_pregnant".
If condition is false:
Proceed to next node (guardrail_high_risk_label).

Node: guardrail_high_risk_label
Purpose:
Add guardrails when the DSI output is high-risk or may strongly influence care.
Example condition:
risk_score >0.8 (or belongs to "high_risk" category).
Example evaluation:
If condition is true:
Set policy.evaluation_outcome="permit_with_guardrails".
Set permit.permit_outcome="permit_with_guardrails".
Append "require_confirmatory_order_review" and "label_high_risk_output" to policy.constraints_applied.
If condition is false:
Set policy.evaluation_outcome="permit".
Set permit.permit_outcome="permit".
In either case, proceed to next node (override_logging).

Node: override_logging
Purpose:
Ensure that clinician overrides are explicitly captured and logged.
Example condition:
Clinician attempts to override a deny outcome or remove applied guardrails.
Example evaluation:
If condition is true:
Require clinician to supply an override_reason_code and, optionally, a free-text justification (reflected via clinician_response.notes_hash).
Set permit.override_required=true.
Set permit.override_type="clinician_explicit_override".
Set clinician_response.override_applied=true and capture the override_reason_code.

If condition is false:

No override is required; evaluation concludes with the prior permit outcome.

Example: Imaging Triage DSI Policy Graph Snippet

For an imaging triage DSI, such as a multi-condition radiology triage model for abdomen-pelvis CT studies, a policy graph may include additional or alternative nodes, for example:

Node: modality_supported
Condition:
context.dsi_metadata.modality="CT" AND context.dsi_metadata.body_region= "abdomen_pelvis".
Action:
If false→set permit.permit_outcome="deny" or route to an appropriate DSI variant.
Node: triage_target_whitelist
Condition:
All triage target classes requested (for example, small_bowel_obstruction, free_air, aortic_aneurysm) belong to an approved target list for the configured policy profile.
Action:
If false→set permit.permit_outcome="deny" and log a configuration incident flag.
Node: guardrail_multi_condition
Condition:
The DSI proposes more than a threshold number of high-priority triage flags for a single study.
Action:
If true→set policy.evaluation_outcome="permit_with_guardrails", require secondary review by a radiologist, and apply constraints in policy. constraints_applied (for example, "require_secondary_radiologist_review").
Node: autonomous_imaging_mode_gate
Purpose:
Control use of autonomous imaging modes (for example, auto-normal chest radiograph labeling or auto-finalization of draft reports) based on site-local validation and governance predicates.
Example condition:
permit.requested_behavior_mode="autonomous_imaging" AND site-local validation and monitoring indicators remain within configured thresholds.
Example evaluation:
If condition is false or thresholds are not satisfied:
Set permit.effective_behavior_mode="decision_support".
Set permit.permit_outcome to "permit_with_guardrails" or "deny", depending on policy.
Append one or more guardrails to policy.constraints_applied (for example, "require_mandatory_human_review").
If condition is true:
Allow the requested autonomous imaging behavior to proceed under the applicable guardrails.
These examples are illustrative only. In various embodiments, policy graphs may include additional nodes governing, for example, institution-specific contraindications, fairness constraints across population segments, or requirements that certain incident flags or Safety Evidence Receipts automatically enqueue a safety review or trigger a policy-graph update. Regardless of the specific nodes or encoding, the safety receipt layer records, in safety receipt 400, at least an identifier of the policy graph and its version, together with the resulting permit outcome (and, in some embodiments, the requested and effective behavior modes) for the DSI episode. Policy graph examples in this Appendix are evidentiary only; the claims and the core Specification define the permit-before-action semantics and fail-closed behavior of the safety receipt layer.

Appendix E—Example Post-Market Monitoring Profiles (Illustrative; Non-Limiting; Evidence-Only)

This Appendix illustrates, in an abbreviated and non-limiting manner, how safety receipts and the insights and monitoring module can be used to implement post-market monitoring profiles for AI-assisted DSIs. These profiles are machine-readable configurations that reference structured safety receipt fields and derived aggregates, and define how usage, performance, fairness, and safety signals are to be monitored over time for one or more DSI families. Profiles are evidentiary only; they do not alter the permit-before-action semantics or fail-closed behavior enforced by the safety receipt layer, and the claims control.

E.1 Purpose and Scope (Illustrative; Non-Limiting)

In some embodiments, a post-market monitoring profile specifies, for a given DSI family (for example, sepsis risk scoring DSIs, multi-condition imaging triage DSIs, or LLM-based discharge planning assistants):

which safety receipt fields and derived aggregates are to be collected for monitoring;

how episodes are to be grouped or stratified (for example, by care setting, clinician role, or population segment);

which aggregation windows (for example, daily, weekly, monthly) are to be used for computing metrics;

which thresholds or patterns in aggregate metrics must trigger a safety review, model update, policy-graph update, or other governance action; and which evidence bundles or summaries are to be provided to institutional governance committees or external authorities, in a privacy-preserving manner.

Post-market monitoring profiles may be represented as configuration objects consumed by the insights and monitoring module and, in some deployments, by external governance engines such as multi-harm Safety Risk Budget Engines, which may treat monitored metrics as features or inputs for safety evaluation. Such external uses are evidentiary only and do not alter the safety receipt layer's gate predicates or permit-before-action semantics.

E.2 Example Profile Structure (Illustrative JSON-Like Schema)

By way of example and not limitation, a post-market monitoring profile may be expressed using a JSON-like structure:

```
{
  "profile_id": "HTI-PMM-Sepsis-Adult/1.0",
  "dsi_family": "sepsis_risk_score",
  "dsi_types": [
    "sepsis_risk_score_v3"
  ],
  "episode_filters": {
    "care_settings": ["ED", "ICU"],
    "population_segments": ["age_18_64","age_65_plus"],
  },
  "monitored_fields": [
    "permit.permit_outcome",
```

-continued

```
    "clinician_response.response_type",
    "clinician_response.override_applied",
    "clinician_response.override_reason_code",
    "monitoring.alert_burden_bucket",
    "monitoring.incident_flags",
    "monitoring.population_segments",
    "anchor.external_digest"
],
"aggregation_windows": {
    "usage_window_days": 7,
    "performance_window_days": 30,
    "fairness_window_days": 90
},
"metrics": {
    "usage": [
        "dsi_invocation_count",
        "invocations_per_100_encounters",
        "distribution_of_permit_outcomes"
    ],
    "oversight": [
        "override_rate_overall",
        "override_rate_by_population_segment",
        "distribution_of_override_reason_codes"
    ],
    "burden": [
        "alert_burden_bucket_distribution",
        "episodes_in_high_alert_burden_bucket"
    ],
    "performance_and_fairness": [
        "incident_flag_rate_overall",
        "incident_flag_rate_by_population_segment",
        "proxy_performance_indicators_from_linked_labels_or_audits"
    ]
},
"review_triggers": {
    "incident_flag_rate_threshold": 0.02,
    "override_rate_shift_threshold": 0.10,
    "alert_burden_high_bucket_threshold": 0.25,
    "fairness_disparity_threshold": 0.10
},
"reporting": {
    "report_cadence_days": 30,
    "governance_recipients": [
        "institutional_safety_committee",
        "dsi_developer_team"
    ],
    "export_formats": [
        "machine_readable_summary",
        "dashboard_view",
        "evidence_bundle_links"
    ]
  }
 }
}
```

The above structure is illustrative only. Implementations may rename, add, or omit fields while remaining in scope, provided that the profile identifies at least: (i) a DSI family or set of DSI types; (ii) a subset of safety receipt fields and derived aggregates to monitor; (iii) aggregation windows and metric definitions; and (iv) threshold conditions or patterns used to trigger governance actions such as safety reviews, model updates, or policy-graph revisions.

E.3 Integration with Safety Receipts and Monitoring Modules

In various embodiments:

The insights and monitoring module consumes safety receipts generated under the permit-before-action and fail-closed semantics of the safety receipt layer and applies one or more post-market monitoring profiles to compute aggregate metrics for each DSI family, DSI type, care setting, or population segment of interest. Metrics may include, for example, frequencies of DSI invocation, distributions of permit outcomes (permit, permit_with_guardrails, require_override, deny), override rates, distributions of clinician_response.

response_type and override_reason_code values, distributions of monitoring.alert_burden_bucket, and frequencies of monitoring.incident_flags.

Profiles may specify that certain population segments, such as those defined by monitoring.population_segments, are to be monitored for fairness and equity, including relative rates of high-risk recommendations, alert burden, overrides, and incident flags across segments. These uses are evidentiary only; the definitions of population segments and the associated fairness criteria are policy-bound and configurable outside the scope of this Specification.

Profiles may specify that certain incident flags or patterns (for example, repeated "near_miss" or "adverse_event" flags associated with a given DSI type, care setting, or population segment) must enqueue a safety review or trigger a temporary modification of the corresponding policy graph (for example, temporarily tightening permit conditions or disabling a DSI variant pending investigation). The mechanics of such governance processes are policy-dependent and may be implemented in external systems; safety receipts and their aggregates provide the evidence required to support these actions.

Profiles may specify different aggregation windows and review cadences for different DSI families (for example, shorter windows and more frequent reviews for high-risk DSIs, longer windows for lower-risk DSIs), and may be updated over time as governance expectations, regulatory guidance, or institutional policies evolve.

E.4 Evidence-Only Nature of Post-Market Monitoring Profiles

Post-market monitoring profiles are defined as evidence-only overlays on top of the core safety receipt layer. They describe how safety receipt data and aggregates are to be used for monitoring, reporting, and governance purposes, but they do not alter the core semantics of the safety receipt layer, including:

the requirement that DSI execution be gated by a permit-before-action mechanism;

the fail-closed behavior when policy evaluation or anchoring preconditions are not satisfied; and the structure and role of safety receipts as proof-of-policy-compliance artifacts.

The scope of the invention remains defined by the claims and the written description in the main body of this Specification. Profiles described in this Appendix are illustrative and non-limiting; functionally equivalent configurations that use safety receipts and aggregates for post-market monitoring while leaving core gate predicates unchanged are within the contemplated scope.

E.5 Example Post-Market Monitoring Profile for Technology-Enabled Chronic Care (Illustrative; Non-Limiting; Evidence-Only)

By way of example and not limitation, a post-market monitoring profile for a chronic-disease DSI family (for example, cardio-renal-metabolic risk DSIs, hypertension titration DSIs, or musculoskeletal rehabilitation planning DSIs) may be expressed as:

```
{
    "profile_id": "HTI-PMM-ChronicCare-CRM/1.0",
    "dsi_family": "chronic_care_dsi",
    "dsi_types": [
        "crm_risk_score_v1",
        "hypertension_titration_assistant_v2"
```

-continued

```
],
"episode_filters": {
    "care_settings": ["outpatient", "home_health","virtual_visit"],
    "population_segments": ["crm_high_risk","hypertension_stage2"]
},
"monitored_fields": [
    "permit.permit_outcome",
    "clinician_response.response_type",
    "clinician_response.override_applied",
    "monitoring.incident_flags",
    "monitoring.population_segments"
],
"aggregation_windows": {
    "usage_window_days": 7,
    "performance_window_days": 30,
    "fairness_window_days": 90
},
"metrics": {
    "usage": [
        "dsi_invocation_count",
        "invocations_per_enrolled_patient",
        "distribution_of_permit_outcomes"
    ],
    "oversight": [
        "override_rate_overall",
        "override_rate_by_population_segment"
    ],
    "safety_and_equity": [
        "incident_flag_rate_overall",
        "incident_flag_rate_by_population_segment"
    ]
},
"review_triggers": {
    "incident_flag_rate_threshold": 0.02,
    "override_rate_shift_threshold": 0.10,
    "fairness_disparity_threshold": 0.10
},
"reporting": {
    "report_cadence_days": 30,
    "governance_recipients": [
        "institutional_chronic_care_committee",
        "dsi_developer_team"
    ],
    "export_formats": [
        "machine_readable_summary",
        "dashboard_view"
    ]
}
}
```

In some deployments, a chronic-care post-market monitoring profile of this type may be instantiated or parameterized specifically to satisfy real-world evidence obligations for national or regional outcomes-based chronic care payment programs, including ACCESS-style programs for technology-enabled chronic-disease services. Such uses remain evidentiary-only overlays on top of the core safety receipt layer and do not alter the permit-before-action semantics, fail-closed behavior, or gate predicates defined in the present Specification; the claims control.

E.6 ACCESS/TEMPO combined profile
```
{
    "profile_id": "HTI-PMM-ACCESS-TEMPO/1.0",
    "dsi_family": "chronic_care_dsi",
    "dsi_types": [
        "crm_risk_score_v1",
        "hypertension_titration_assistant_v2"
    ],
    "episode_filters": {
        "care_settings": ["outpatient", "home_health", "virtual_visit"],
        "population_segments": ["crm_high_risk", "hypertension_stage2"]
    },
    "monitored_fields": [
        "program.chronic_care_program_id",
```

-continued

```
    "program.outcome_window_days",
    "program.outcome_measure_refs",
    "program.tempo_device_study_id",
    "permit.permit_outcome",
    "monitoring.incident_flags",
    "monitoring.population_segments",
    "anchor.external_digest"
],
"aggregation_windows": {
    "usage_window_days": 7,
    "performance_window_days": 30,
    "fairness_window_days": 90
},
"metrics": {
    "usage": [
        "dsi_invocation_count",
        "invocations_per_enrolled_patient",
        "distribution_of_permit_outcomes"
    ],
    "safety_and_equity": [
        "incident_flag_rate_overall",
        "incident_flag_rate_by_population_segment"
    ],
    "rwe": [
        "episodes_with_valid_program_metadata",
        "episodes_with_completed_outcome_window"
    ]
},
"reporting": {
    "report_cadence_days": 90,
    "governance_recipients": [
        "institutional_chronic_care_committee",
        "payer_or_program_sponsor"
    ],
    "export_formats": [
        "machine_readable_summary",
        "evidence_bundle_links"
    ]
}
}
```

This ACCESS/TEMPO combined profile is an evidentiary-only monitoring overlay for technology-enabled chronic care and digital health pilots; it leverages safety receipts and the optional program object as canonical evidence objects for outcomes-based payment and real-world evidence obligations, without altering the permit-before-action semantics, fail-closed behavior, or gate predicates defined in the core Specification; the claims control.

The invention claimed is:

1. A computer-implemented method comprising:

intercepting, by a safety receipt layer interposed between an electronic health record (EHR) system and a clinical decision support intervention (DSI) engine, a DSI request for a DSI episode, the DSI request comprising patient data from the EHR system;

constructing, by the safety receipt layer, a clinical context envelope representing a subset of the patient data and one or more DSI metadata fields;

evaluating, by a policy graph evaluation engine of the safety receipt layer, a policy graph over the clinical context envelope to determine a permit outcome for the DSI episode;

gating, by a permit decision engine of the safety receipt layer, execution of the DSI engine based at least in part on the permit outcome, including enforcing permit-before-action and fail-closed semantics for rendering an AI-assisted clinical recommendation to a clinician or for initiating any DSI-initiated write-back to the EHR system; and generating, by a safety receipt generator of the safety receipt layer, a structured, machine-verifiable safety receipt for the DSI episode, the structured, machine-verifiable safety receipt comprising data representing at least: (i) the clinical context envelope or a crypto-graphic digest of a canonicalized listing of fields of the clinical context envelope, (ii) the policy graph or an identifier of the policy graph, and (iii) the permit outcome.

2. The method of claim 1, further comprising transmitting, by a proof-of-policy-compliance (PoPC) anchor client, at least a portion of the structured, machine-verifiable safety receipt or a cryptographic digest thereof to a tamper-evident audit store comprising an append-only verifiable log configured to publish signed heads under a maximum-merge-delay freshness policy and to expose inclusion proofs and consistency proofs, and treating successful transmission and verification of an inclusion proof against a fresh signed head as an anchoring precondition for finalizing or delivering the AI-assisted clinical recommendation.

3. The method of claim 1, further comprising computing the permit outcome as one of:
permit, permit with guardrails, require override, or deny.

4. The method of claim 1, further comprising:
receiving, at the safety receipt layer, a clinician response to the AI-assisted clinical recommendation, the clini-cian response indicating an override type and one or more override reason codes associated with an over-ride-permitted outcome and, when present, a secondary authentication identifier associated with a secondary authentication event; and
encoding, in the structured, machine-verifiable safety receipt, data representing the clinician response, including the override type, the one or more override reason codes, and the secondary authentication identi-fier.

5. The method of claim 1, wherein constructing the clinical context envelope comprises including at least: one or more diagnosis codes or problem list entries, one or more vital signs or laboratory results, one or more active medi-cations, a clinician role or user identifier, and a DSI type identifier.

6. The method of claim 1, wherein evaluating the policy graph comprises evaluating the policy graph based at least in part on the one or more DSI metadata fields, the one or more DSI metadata fields comprising at least one of: a DSI type identifier; a model identifier, a DSI family identifier, a version identifier, or a configuration identifier; a transpar-ency profile identifier or a profile identifier associated with the DSI engine or a deployment thereof; a risk-tier indicator, a hazard classification, a change-control identifier, or a mitigation-status indicator associated with the DSI type or model configuration; a deployment identifier, a tenant iden-tifier, or a site identifier; a requested behavior mode; or a site-local validation indicator, a monitoring indicator, or a governance-status indicator associated with the DSI engine or a deployment thereof.

7. The method of claim 1, further comprising operating the permit decision engine to enforce fail-closed behavior by preventing finalization of both (i) rendering the AI-assisted clinical recommendation to a clinician and (ii) any DSI-initiated write-back of orders or documentation to the EHR system for the DSI episode unless the permit outcome satisfies a permit condition and an anchoring precondition, and enforcing a time-of-check-to-time-of-use latch binding policy evaluation and any anchoring precondition to render and write-back finalization.

8. The method of claim 7, further comprising generating, by the safety receipt generator, a failure-mode safety receipt encoding a structured reason code when the permit outcome does not satisfy the permit condition.

9. The method of claim 1, further comprising encoding, in the structured, machine-verifiable safety receipt: (i) an explicit listing of electronic health record fields and clinical decision support intervention metadata fields included in the clinical context envelope, and (ii) a cryptographic digest of that listing, and exposing a verification interface configured, given EHR and DSI logs for the DSI episode, to recompute the listing and the cryptographic digest using deterministic canonicalization rules and confirm that the permit outcome was generated from that clinical context envelope.

10. The method of claim 1, wherein constructing the clinical context envelope and generating the structured, machine-verifiable safety receipt further comprise encoding, in the structured, machine-verifiable safety receipt: (i) a requested imaging behavior mode, (ii) an effective imaging behavior mode, and (iii) the permit outcome for an imaging triage DSI episode.

11. The method of claim 1, further comprising enforcing a permit validity interval and a revocation mechanism, wherein expiration of a recorded permit validity interval or presence of an active revocation identifier causes the safety receipt layer to deny finalization of render or write-back for the DSI episode under fail-closed semantics, and to emit a failure-mode safety receipt.

12. A non-transitory computer-readable medium storing instructions that, when executed by one or more processors, cause a system to:
intercept, by a safety receipt layer interposed between an electronic health record (EHR) system and a clinical decision support intervention (DSI) engine, a DSI request for a DSI episode, the DSI request comprising patient data from the EHR system;
construct a clinical context envelope representing a subset of the patient data and one or more DSI metadata fields;
evaluate a policy graph over the clinical context envelope to determine a permit outcome for the DSI episode;
gate execution of the DSI engine based at least in part on the permit outcome, including enforcing permit-before-action and fail-closed semantics for rendering an AI-assisted clinical recommendation to a clinician or for initiating any DSI-initiated write-back to the EHR system; and
generate a structured, machine-verifiable safety receipt for the DSI episode, the structured, machine-verifiable safety receipt comprising data representing at least: (i) the clinical context envelope or a cryptographic digest of a canonicalized listing of fields of the clinical context envelope, (ii) the policy graph or an identifier of the policy graph, and (iii) the permit outcome.

13. The non-transitory computer-readable medium of claim 12, wherein the instructions, when executed, further cause the system to transmit at least a portion of the structured, machine-verifiable safety receipt or a crypto-graphic digest thereof to a tamper-evident audit store com-prising an append-only verifiable log configured to publish signed heads under a maximum-merge-delay freshness policy and to expose inclusion proofs and consistency proofs, and to treat successful transmission and verification of an inclusion proof against a fresh signed head as an anchoring precondition for finalizing or delivering the AI-assisted clinical recommendation.

14. The non-transitory computer-readable medium of claim 12, wherein the instructions, when executed by one or more processors, further cause the system to enforce a time-of-check-to-time-of-use latch binding policy evaluation and any anchoring precondition to render and write-back finalization for the DSI episode, and to apply an idempotency mechanism configured to ensure atomic finalization of render and write-back for the DSI episode across retries, the idempotency mechanism comprising at least one of: an idempotency token, a transaction fence, a compare-and-swap-based commit marker, a write-ahead-log barrier, or a functionally equivalent control mechanism that prevents duplicate or split-brain finalizations across retries.

15. The non-transitory computer-readable medium of claim 12, wherein the instructions, when executed, further cause the system to encode, in the structured, machine-verifiable safety receipt: (i) an explicit listing of electronic health record fields and clinical decision support intervention metadata fields included in the clinical context envelope, and (ii) a cryptographic digest of that listing, and to provide a verification interface configured, given EHR and DSI logs for the DSI episode, to recompute the listing and the cryptographic digest using deterministic canonicalization rules and confirm that the permit outcome was generated from that clinical context envelope.

16. The non-transitory computer-readable medium of claim 12, wherein the instructions, when executed, further cause the system to operate the safety receipt layer over an agentic clinical workflow in which one or more autonomous or semi-autonomous software agents orchestrate multiple DSI steps, retrieval operations, or documentation steps for an episode of care, and to treat each DSI step as a bounded DSI episode or sub-episode subject to the same permit-before-action and fail-closed semantics enforced by the safety receipt layer.

17. A system comprising:
an electronic health record (EHR) system configured to store patient data;
a clinical decision support intervention (DSI) engine configured to receive patient data from the EHR system and to output a clinical recommendation, including AI-assisted clinical recommendations, based at least in part on the patient data; and
a safety receipt layer interposed between the EHR system and the DSI engine for a DSI episode, the safety receipt layer comprising:
a context capture module configured to construct, responsive to an invocation of the DSI engine for the DSI episode, a clinical context envelope representing a subset of the patient data and one or more DSI metadata fields associated with the DSI engine;
a policy graph evaluation engine configured to evaluate a policy graph over the clinical context envelope to determine a permit outcome for the DSI episode;
a permit decision engine configured to gate execution of the DSI engine based at least in part on the permit outcome, including enforcing permit-before-action and fail-closed semantics for rendering the AI-assisted clinical recommendations to a clinician or for initiating any DSI-initiated write-back to the EHR system; and
a safety receipt generator configured to generate a structured, machine-verifiable safety receipt for the DSI episode, the structured, machine-verifiable safety receipt comprising data representing at least: (i) the clinical context envelope or a cryptographic digest of a canonicalized listing of fields of the clinical context envelope, (ii) the policy graph or an identifier of the policy graph, and (iii) the permit outcome.

18. The system of claim 17, further comprising a proof-of-policy-compliance (PoPC) anchor client configured to transmit at least a portion of the structured, machine-verifiable safety receipt or a cryptographic digest thereof to a tamper-evident audit store comprising an append-only verifiable log that publishes signed heads subject to a maximum-merge-delay freshness policy and exposes inclusion proofs and consistency proofs; wherein the permit decision engine is further configured to treat successful transmission by the PoPC anchor client, including verification of an inclusion proof against a fresh signed head under the maximum-merge-delay freshness policy, as an anchoring precondition for finalizing or delivering the AI-assisted clinical recommendation; and wherein the structured, machine-verifiable safety receipt further encodes a status tuple comprising at least a signed_head_id, a head_timestamp, and a staleness_interval derived from the anchoring event and the maximum-merge-delay freshness policy, the status tuple being configured to enable verification of log freshness and anchoring integrity at review time.

19. The system of claim 17, wherein the policy graph evaluation engine is further configured to classify the permit outcome into one of: permit, permit with guardrails, require override, or deny.

20. The system of claim 17, wherein the permit decision engine is configured to enforce a time-of-check-to-time-of-use latch binding policy evaluation and any anchoring precondition to render and write-back finalization for the DSI episode; to apply an idempotency mechanism configured to ensure atomic finalization of render and write-back for the DSI episode across retries, the idempotency mechanism comprising at least one of: an idempotency token, a transaction fence, a compare-and-swap-based commit marker, a write-ahead-log barrier, or a functionally equivalent control mechanism that prevents duplicate or split-brain finalizations across retries; and to enforce fail-closed behavior unless (i) the permit outcome satisfies a permit condition and (ii) any applicable anchoring precondition is satisfied.

21. The system of claim 17, wherein the clinical context envelope comprises at least: (i) one or more diagnosis codes or problem list entries, (ii) one or more vital signs or laboratory results, (iii) one or more active medication orders, (iv) a clinician role or user identifier, and (v) a DSI type identifier associated with the DSI engine.

22. The system of claim 17, wherein the safety receipt generator is further configured to include, in the structured, machine-verifiable safety receipt, data representing a clinician response to the AI-assisted clinical recommendation, including any override type and one or more override reason codes associated with an override-permitted outcome and, when present, a secondary authentication identifier associated with a secondary authentication event required to complete the override.

23. The system of claim 17, wherein the safety receipt generator is further configured to encode the structured, machine-verifiable safety receipt in a machine-readable serialization format comprising defined fields mapped to one or more health information technology transparency or certification requirements, including at least (i) a DSI transparency profile identifier and (ii) either a framework profile identifier or a reference to associated transparency documentation for the DSI engine, such that the structured, machine-verifiable safety receipt can be interpreted both as a permit-before-action execution record and as machine-readable evidence of conformance to one or more transparency or certification frameworks.

24. The system of claim 17, wherein the policy graph evaluation engine is configured to evaluate the policy graph based at least in part on the one or more DSI metadata fields, the one or more DSI metadata fields comprising at least one of: a DSI type identifier; a model identifier, a DSI family identifier, a version identifier, or a configuration identifier; a transparency profile identifier or a profile identifier associated with the DSI engine or a deployment thereof; a risk-tier indicator, a hazard classification, a change-control identifier, or a mitigation-status indicator associated with the DSI type or model configuration; a deployment identifier, a tenant identifier, or a site identifier; a requested behavior mode; or a site-local validation indicator, a monitoring indicator, or a governance-status indicator associated with the DSI engine or a deployment thereof.

25. The system of claim 17, wherein the structured, machine-verifiable safety receipt further comprises data representing: (i) an explicit listing of electronic health record fields and clinical decision support intervention metadata fields included in the clinical context envelope, and (ii) a cryptographic digest of that listing, and wherein the safety receipt layer exposes a verification interface configured, given EHR and DSI logs for the DSI episode, to recompute the listing and the cryptographic digest using deterministic canonicalization rules and to confirm that the permit outcome was generated from that clinical context envelope.

26. The system of claim 17, wherein the structured, machine-verifiable safety receipt further comprises one or more cross-rail references to external governance receipts, including at least one of: a sensor receipt emitted by a trusted sensor ingress rail, a reality receipt emitted by a trusted reality compositor, a safety evidence receipt emitted by a safety risk budget engine, or a revenue-cycle governance receipt, and wherein the cross-rail references are evidentiary only and do not alter the safety receipt layer's gate conditions, permit outcomes, permit-before-action semantics, or fail-closed behavior.

27. The system of claim 17, wherein the DSI engine comprises an imaging triage DSI configured to process medical images and output imaging behavior modes including at least a decision-support imaging behavior mode and an autonomous or semi-autonomous imaging behavior mode, and wherein the permit decision engine is further configured to gate entry into the autonomous or semi-autonomous imaging behavior mode based at least in part on site-local validation indicators and the permit outcome, and wherein the structured, machine-verifiable safety receipt further comprises data representing a requested imaging behavior mode and an effective imaging behavior mode for the DSI episode.

28. The system of claim 17, wherein the safety receipt layer is further configured to operate over an agentic clinical workflow in which one or more autonomous or semi-autonomous software agents orchestrate multiple DSI steps, retrieval operations, or documentation steps for an episode of care, and wherein each step is treated as a bounded DSI episode or sub-episode subject to the same permit-before-action and fail-closed semantics enforced by the safety receipt layer, and the structured, machine-verifiable safety receipt further comprises data indicating at least a workflow identifier and a step identifier linking the DSI episode to the agentic clinical workflow.

29. The system of claim 17, wherein patient, encounter, and organization identifiers encoded in the structured, machine-verifiable safety receipt are pseudonymous identifiers derived via a per-tenant keyed HMAC (hash-based message authentication code), enabling cross-receipt linkage for oversight and analytics without exposing direct identifiers.

30. The system of claim 17, wherein the structured, machine-verifiable safety receipt further comprises a policy_digest and, optionally, a policy_signature over the policy graph or policy profile used to compute the permit outcome.

* * * * *